(12) United States Patent
Iwamiya et al.

(10) Patent No.: US 7,314,450 B2
(45) Date of Patent: Jan. 1, 2008

(54) WEARABLE HEARTBEAT MEASURING DEVICE, SYSTEM AND METHOD

(75) Inventors: Hiroshi Iwamiya, Ome (JP); Mituru Kainuma, Kawasaki (JP); Kazuo Aoki, Yokohama (JP); Kazuto Ushiyama, Ome (JP)

(73) Assignees: Casio Computer Co., Ltd., Tokyo (JP); Otax Co., Ltd., Kanagawa (JP)

( * ) Notice: Subject to any disclaimer, the term of this patent is extended or adjusted under 35 U.S.C. 154(b) by 220 days.

(21) Appl. No.: 10/926,894

(22) Filed: Aug. 26, 2004

(65) Prior Publication Data

US 2005/0049514 A1    Mar. 3, 2005

(30) Foreign Application Priority Data

Aug. 29, 2003  (JP) ............................. 2003-209554
Nov. 14, 2003  (JP) ............................. 2003-385271

(51) Int. Cl.
*A61B 5/02*    (2006.01)

(52) U.S. Cl. ................... 600/503; 600/481; 600/500

(58) Field of Classification Search ................ 600/503; 368/282; 24/265 B
See application file for complete search history.

(56) References Cited

U.S. PATENT DOCUMENTS

| 5,243,992 A * | 9/1993 | Eckerle et al. ............ 600/503 |
| 5,941,828 A * | 8/1999 | Archibald et al. .......... 600/494 |
| 2001/0020134 A1* | 9/2001 | Nissila et al. ............ 600/503 |
| 2004/0243009 A1 | 12/2004 | Tanaka et al. |

FOREIGN PATENT DOCUMENTS

| JP | 62-161344 A | 7/1987 |
| JP | 62-292137 | 12/1987 |
| JP | 8-215163 A | 8/1996 |
| JP | 08-299292 | 11/1996 |
| JP | 9-294727 A | 11/1997 |

(Continued)

OTHER PUBLICATIONS

JP Office Action dated Oct.17, 2006. [English Abstract].

(Continued)

*Primary Examiner*—Charles A. Marmor, II
*Assistant Examiner*—Patricia C. Mallari
(74) *Attorney, Agent, or Firm*—Knoble Yoshida & Dunleavy, LLC

(57) ABSTRACT

The wearable heartbeat measuring device is accomplished by wearing a wrist-watch-like heart monitor device on the wrist. The heart monitor is worn on the top of the wrist with a strap around the wrist. The strap has an inflexible extending portion that extends from the heart monitor at a predetermined angle and a predetermined width with respect to the wrist so that a predetermined space is maintained between the top portion of the wrist and the strap for promoting the transfer efficiency of the pulsation force that is initially experienced at a part of the strap at the bottom of the wrist. The strap also has a flexible portion. A predetermined angle and a predetermined width of the extended portion also facilitate the flexible portion to form a flat area where the wrist contacts the strap. In the prefer embodiments, the width of the strap exceeds the width of the wrist when it is worn.

20 Claims, 16 Drawing Sheets

FOREIGN PATENT DOCUMENTS

| | | |
|---|---|---|
| JP | 2000-237152 A | 9/2000 |
| JP | 2001-78972 A | 3/2001 |
| JP | 2001-78973 A | 3/2001 |
| JP | 2002-78689 A | 3/2002 |
| JP | 2003-126049 A | 5/2003 |
| JP | 2005-590 A | 1/2005 |

OTHER PUBLICATIONS

JP Office Action dated Mar. 13, 2007. [English Abstract].

* cited by examiner

WEARABLE HEARTBEAT MEASURING DEVICE, SYSTEM AND METHOD

FIELD OF THE INVENTION

The current invention is generally related to a wearable heartbeat measuring device, and more particularly related to a wrist watch containing a two-room chamber heartbeat measuring device that can be worn around the wrist.

BACKGROUND OF THE INVENTION

Portable heart monitors and blood pressure monitors have been known. Some of these monitors incorporate watch functions and are worn on the wrist of the user. The display on the watch indicates time and or date. Furthermore, the user selects a certain mode to monitor either blood pressure or heartbeat. For example, as disclosed in Japanese Patent Publication Hei 8-299292, after the user selects a heartbeat monitor mode, the display indicates a number of heartbeats per minute. However, to measure heartbeats, a small cuff must be additionally worn on a finger tip by the user.

Japanese Publication 62-292137 discloses another example of a blood pressure monitor. A wrist watch incorporates a blood pressure monitor. An inflatable tubular cuff has been incorporated in the wrist band or the straps. The cuff is connected to a pressure measuring chamber, and a pressure sensor is located in the pressure chamber. Upon selecting a blood pressure measuring mode, the user manually pumps air into the cuff in order to inflate the cuff against the arteries in the wrist. The intermittently inflated cuff contains air whose pressure is measured by the pressure sensor. The measured pressure change is calculated to display the blood pressure at the display.

As described above, in prior art, to measure either blood pressure or heartbeat, the user must perform additional tasks. According to the above examples, the user must wear an additional finger piece for the heartbeat measurement or must pump the air into the cuff for the blood pressure measurement.

In addition, the above described prior,art techniques also encounter noise. One source of the noise is associated with the movements of the wrist. In order to measure the blood pressure, the cuff must be sufficiently inflated around the entire circumference of the wrist so as to detect the pressure change in the arteries. Because of the snug contact, certain wrist movements also cause undesirable and indistinguishable pressure change. Another source of the noise is associated with small high-frequency components that are not caused by arterial movement.

For the above reasons, it remains desired to develop a method, device and system to measure the arterial movement by a wearable watch device without any additional component and at a high accuracy.

SUMMARY OF THE INVENTION

In order to solve the above and other problems, according to a first aspect of the current invention, a wearable heartbeat measuring device, including: a heartbeat detection unit for detecting an arterial movement indicative of a heartbeat around the wrist to generate a heartbeat signal; and a wrist strap for supporting the heartbeat detection unit near a top portion of thewrist, said wrist strap having a flexible portion and an inflexible portion, the inflexible portion extending from the heartbeat detection unit and havung a predetermined angle and a predetermined width with respect to the wrist so as to form a predetermined amount of space between the wrist and the strap near the top portion of the wrist, the inflexible portion further including a first adjustable portion having a plurality of holes and a pin for adjusting the width.

According to the second aspect of the current invention, a wearable heartbeat measuring device, including: a heartbeat detection unit for detecting an arterial movement indicative of a heartbeat around the wrist to generate a heartbeat signal; and a wrist strap for supporting the heartbeat detection unit near a top portion of the wrist, the wrist strap having a flexible portion and an inflexible portion, the inflexible portion extending from the heartbeat detection unit and having a predetermined angle and a predetermined width that exceeds the wrist so as to form a predetermined amount of space between the wrist and the strap near the top portion of the wrist, the inflexible portion further including a first adjustable portion having a plurality of holes and a pin for adjusting the widtth.

According to the third aspect of the current invention, a heartbeat detection device, including: a first unit having a first flexible enclosed area for forming a first chamber, a pressure in the first chamber changing in response to an externally applied pressure, the first unit further including an inflexible plate mounted on a surface where the externally applied pressure is exerted; a second unit having a second enclosed area located adjacent to the first chamber for forming a second chamber, the second chamber having a pressure sensitive element for generating a signal indicative of a pressure change; and a separation wall located between the first unit and said second unit, the separation wall having a communication hole for connecting the first chamber and the second chamber.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Based upon incorporation by external reference, the current application incorporates all disclosures in the corresponding foreign priority documents (2003-209554, 2003-385271) from which the current application claims priority.

Figure 1:
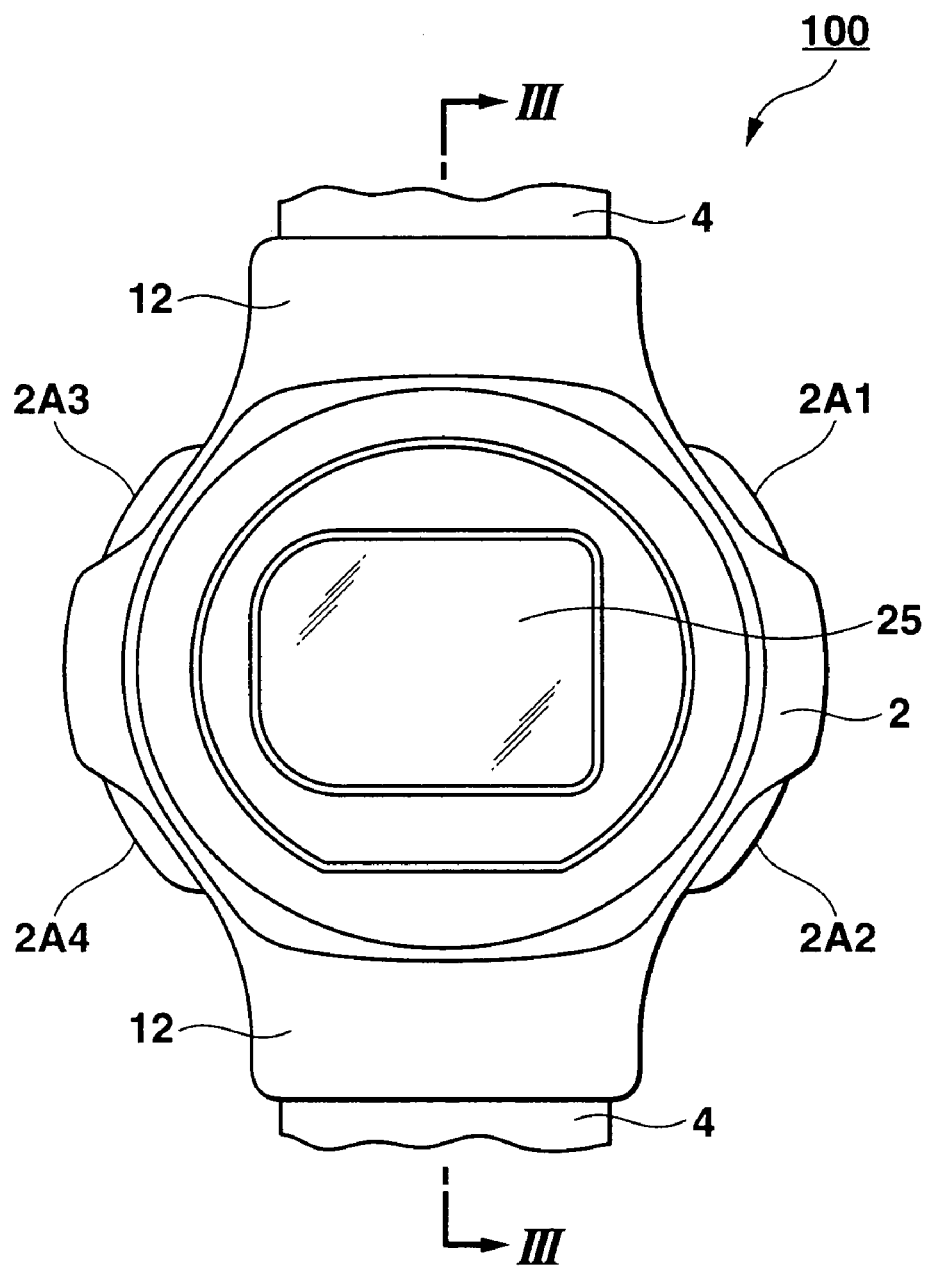
FIG. 1 is a diagram illustrating a front view of one preferred embodiment of a heartbeat measuring watch device according to the current invention.

Referring now to the drawings, wherein like reference numerals designate corresponding structures throughout the views, and referring in particular to FIG. 1, a diagram illustrates a front view of one preferred embodiment of a heartbeat measuring watch device 100 according to the current invention. The heartbeat measuring watch device 100 includes a watch casing or housing 2 and a strap or belt 4 removably placing around the wrist of a user. One end of each of the two straps 4 is connected at a protruding portion or extended casing portion 12 of the watch casing 2, and the other end of the straps 4 is removably connectable with each other via a clasp or some other means that are not illustrated in FIG. 1. The extended casing portion 12 extends away from an edge of the casing 2 around the wrist to provide a certain width to the casing 2. The above casing width allows the user to strap the heartbeat measuring watch device 100 around the wrist via the straps 4 in a certain manner as will be described later with respect to cross sectional view. In the following preferred embodiments including this one, the width of the straps 4, the casing 2 and the extended casing portion 12 or their equivalents is defined to be a combined width of the straps 4, the extended casing portion 12 and the casing 2 or their equivalents in the strapping direction along a line III-III when viewed from top as shown in FIG. 1. Although the straps 4 are bendable, they are made of certain non-stretchable material so that force caused by the pulse or heartbeat around the wrist is transmitted through the straps 4 when the straps 4 are worn around the wrist in a sufficiently tight manner.

Still referring to FIG. 1, the heartbeat measuring watch device 100 further includes a display unit 25 for displaying various information. The display unit 25 is implemented by a display device such as a liquid crystal display (LCD) and is mounted on or in the casing 2. The information includes certain combinations of information on time, date, heartbeat and predetermined others. The information is also selected by the user command via selection keys or switches 2A1 through 2A4. A certain predetermined combinations of the selection keys 2A1 through 2A4 allows the user to adjust the information such as time and date, to initiate a desired command such as a heartbeat measurement process or to respond to a message displayed on the heartbeat measuring watch device 100. Although four selection keys 2A1 through 2A4 are shown in this preferred embodiment, a number of the selection keys is not limited to a certain number according to the current invention. Furthermore, the display unit 25 is optionally lit in response to a user command or a light level so that the displayed information is read in the dark.

Figure 2:
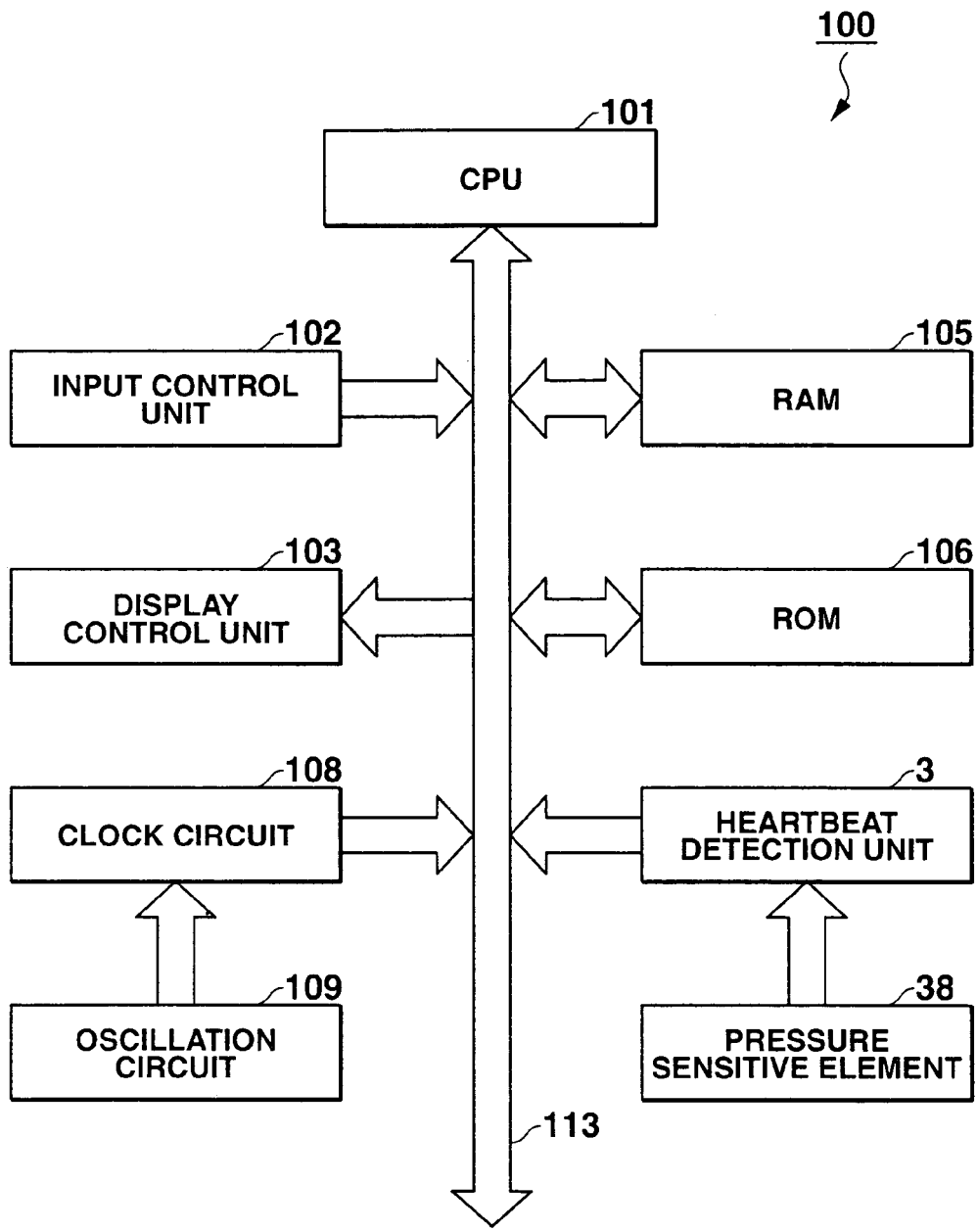
FIG. 2 is a block diagram illustrating certain components of the heartbeat measuring watch device according to the current invention.

FIG. 2 is a block diagram illustrating certain components of the heartbeat measuring watch device 100 according to the current invention. The following predetermined elements or units are located in or around the casing 2 of the heartbeat measuring watch device 100. In general, a central processing unit (CPU) 101 receives an input from a user via an input control unit 102 and initiates a certain corresponding task by executing a predetermined software program in a random access memory (RAM) 105. In other situations, the CPU 101 instructs a display control unit 103 to output a display. In response to the display output, the user inputs a command. The software programs include system/application programs for keeping time and data as well as for measuring the heartbeat. These programs are stored in a read only memory (ROM) 106, and the CPU 101 reads a software program into the RAM 105 in response to a certain command. One of the user commands is to initiate a heartbeat measurement at a heartbeat detection unit or heart monitor 3. After the heartbeat detection unit 3 receives signals from a pressure sensitive element 38, the heartbeat detection unit 3 sends the data to the CPU 101 and the corresponding heartbeat measurement software program. Upon completing the heartbeat measurement, the CPU 101 selectively instructs the display control unit 103 to display the measurement result. An oscillator 109 generates an oscillation signal for the watch function. The oscillation signal is inputted into a clock circuit 108, and the CPU also selectively instructs the display control unit 103 to output the time and or date information. The above mentioned units or components except for the oscillation circuit 109 and the pressure sensitive element 38 are directly connected with each other via a common bus 113.

Figure 3:
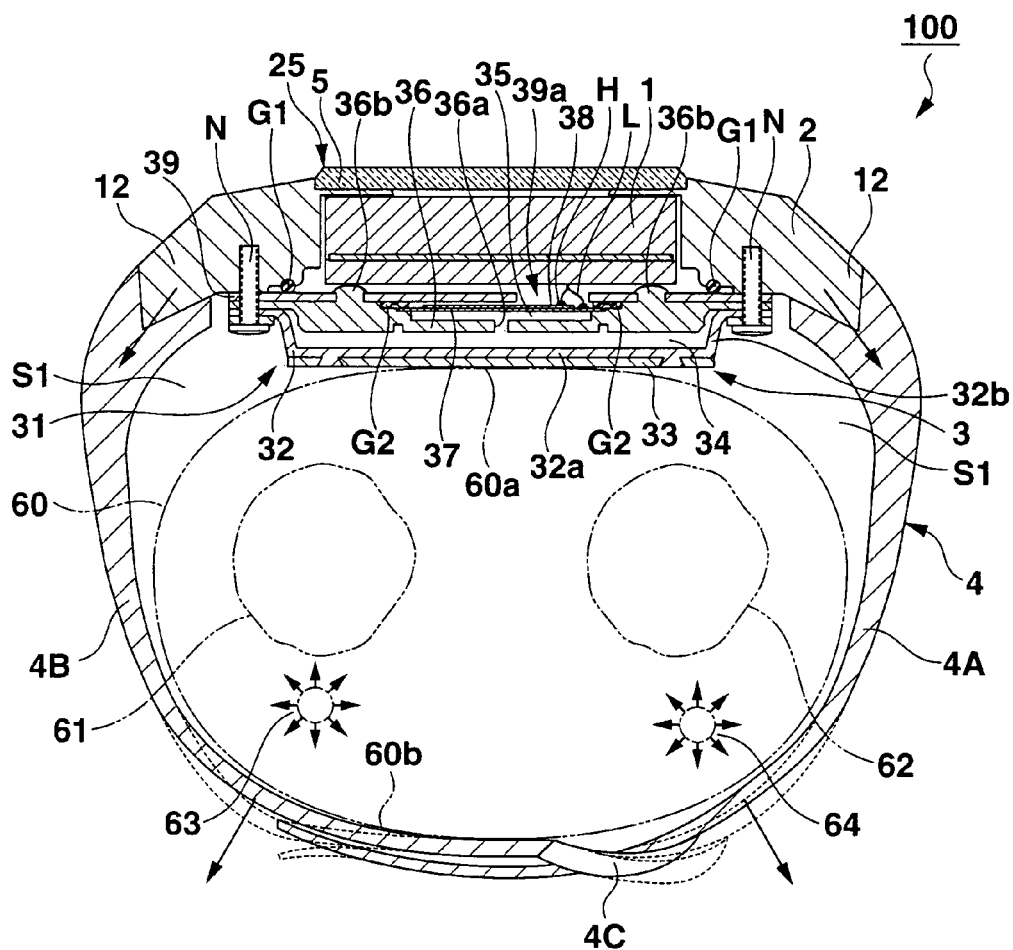
FIG. 3 is a diagram illustrating a cross sectional view along a line III-III of FIG. 1 of the heartbeat measuring watch device in a first preferred embodiment according to the current invention.

Now referring to FIG. 3, a diagram illustrates a cross sectional view along a line III-III of FIG. 1 of the heartbeat measuring watch device 100 in a first preferred embodiment according to the current invention. The heartbeat detection unit 3 is mounted on a bottom surface of the time keeping unit I that is located in the inflexible or hard casing body 2. On the top surface of the time keeping unit 1, a display unit 25 is covered by a transparent watch display cover or glass 5. The heartbeat detection unit 3 is fixed to the casing 2 by components N such as screws via rubber rings G1. Edges of the casing 2 are respectively connected to one end of flexible straps 4A and 4B via an extended casing portion 12. In general, the straps 4A and 4B are made of flexible, but non-expandable material such as certain silicon, leather or silicon to fit the curvature of the wrist 60 without expansion. The other end of the straps 4A and 4B has a fastening mechanism 4C such as a buckle to engage with each other so that the heartbeat measuring watch device 100 is adjustably worn around a wrist 60. Thus, the heartbeat detection unit 3 contacts the upper portion or top portion 60a of the user wrist 60 when the heartbeat measuring watch device 100 is worn as indicated in FIG. 3.

In further detail, the heartbeat measuring watch device 100 detects the heartbeat from the wrist 60. In the wrist 60, the ulnar artery 63 and the radial artery 64 are respectively located below the ulna 61 and the radius 62 and are positioned near a bottom portion of the joined straps 4A and 4B or the fastening mechanism 4C. The two arteries 63 and 64 are substantially perpendicular to the strapping direction of the straps 4A and 4B. As the two arteries 63 and 64 expand as indicated by the dotted lines, the expansion causes the pulsation force in certain directions as indicated by the arrows. Subsequently, as the two arteries 63 and 64 contract, the above expansion force rebounds as a reactive force, and the straps 4A and 4B thus experience a pulsation force. A part of the repeating pulsation force then travels along the straps 4A and 4B towards the heartbeat detection unit 3 via the extended casing portion 12 and the casing 2.

The extended casing portion 12 extends from the casing 2 at a predetermined angle as indicated by an arrow in order to provide an additional width or horizontal dimension to the casing 2. The predetermined angle and the width of the extended casing portion 12 substantially facilitate the flexible straps 4A and 4B to form a relatively flat portion near the fastening mechanism 4C in order to ascertain snug contact over the bottom portion 60b of the wrist 60 for efficiently initiating the transfer of the pulsation force. The predetermined angle and the predetermined width of the extended casing portion 12 also form the space S1 with the casing 2, the straps 4A and 4B and an upper portion or top portion 60a of the wrist 60 near the heartbeat detection unit 3. Because the extended casing portion 12 is made of hard material, the flexing movement of the wrist 60 is confined in the space S1, and the upper side portions of the wrist 60 fail to touch the corresponding upper side area of the flexible straps 4A and 4B. The lack of the above skin contact also substantially promotes the efficient transfer of the pulsation force along the straps 4A and 4B towards the heartbeat detection unit 3. Thus, the total width of the casing 2, the extended casing portion 12 and the straps 4A and 4B exceeds the width of the wrist 60 in the first preferred embodiment.

Still referring to FIG. 3, the heartbeat detection unit 3 detects the pulsation force that is caused by the arterial expansion and contraction in the wrist 60. The heartbeat detection unit 3 further includes a first chamber 34 and a second chamber 35. Although the first chamber 34 and the second chamber 35 are connected by a communication hole 36a, they are substantially separated by a separation wall 36. The communication hole 36a is located at a substantially central portion of the separation wall 36. A top or ceiling wall of the second chamber 35 is formed by a partially overlapping layer of a pressure sensitive element 38 and a metallic plate 37. A part of the overlapping layer is sandwiched between the separation wall 36 and a panel wall 39 via rubber rings G2. The panel wall 39 has an opening portion 39a, through which lead wires L access the pressure sensitive element 38 and the metallic plate 37. The separation material 36 further includes air-tight protruding portions 36b that extend through the panel wall 39 in order to maintain the internal pressure in the second chamber 35 by pressing the panel wall 39 against the rubber rings G2. The air-tight protruding portions 36b are fused or affixed to the panel wall 39. The first chamber 34 projects towards the wrist 60. A bottom or floor wall 32a and side walls 32b of the first chamber 34 are uniformly or integrally formed by a projection unit 32. The 30 bottom wall 32a is plated by an inflexible plate 33 such as certain hard metal. The projection unit 32 is made of a certain flexible insulation material 31 such as urethane, silicon or synthetic rubber. The insulation material 31 maintains the internal pressure in the first chamber 34. An edge portion of the projection unit 32, the separation wall 36 and the panel wall 39 are screwed together to the casing 2 by a screw N in order to maintain the internal pressure of the heartbeat detection unit 3. To further maintain the internal pressure of the casing 2, the above screwed edge portions are pressed against the rubber rings G1 located near the screw N.

Figure 4:
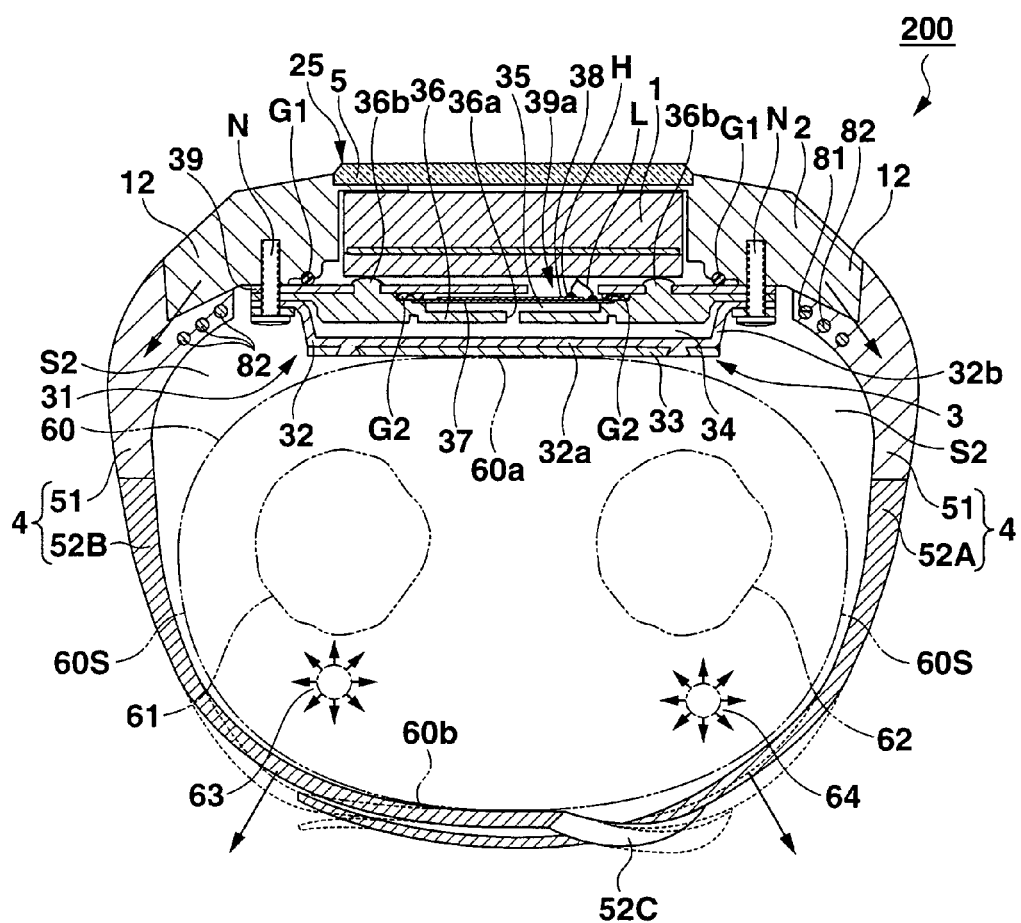
FIG. 4 is a diagram illustrating a cross sectional view of the heartbeat measuring watch device in a second preferred embodiment according to the current invention.

Now referring to FIG. 4, a diagram illustrates a cross sectional view of the heartbeat measuring watch device 200 in a second preferred embodiment according to the current invention. The heartbeat detection unit 3 is mounted on a bottom surface of the time keeping unit 1 that is located in the inflexible or hard casing body 2. On the top surface of the time keeping unit 1, a display unit 25 is covered by a transparent watch display cover 5. The heartbeat detection unit 3 is fixed to the casing 2 by components N such as screws via rubber rings G1. An extended casing portion 12 extends from the casing 2 at a predetermined angle as indicated by an arrow in order to provide an additional width or horizontal dimension to the casing 2. The extended casing portion 12 then connects to an adjustably extended casing portion 51, which is made of inflexible material such as hard resin or metal in order to further adjust the width or horizontal dimension. The adjustably extended casing portion 51 further includes a connecting pin 82 and a plurality of connecting holes 81 for adjusting the width with respect to the wrist 60 of a user. The other end of the adjustably extended casing portions 51 is respectively connected to one end of straps 52A and 52B that are made of flexible, but non-expandable material such as certain silicon or resin to fit the curvature of a wrist 60 without expansion. The other end of the straps 52A and 52B has a fastening mechanism 52C such as a buckle to engage with each other so that the heartbeat measuring watch device 200 is adjustably worn around the wrist 60. Thus, the heartbeat detection unit 3 contacts the upper portion or top portion 60a of the user wrist 60 when the heartbeat measuring watch device 200 is worn as indicated in FIG. 4.

In the further detail, the heartbeat measuring watch device 100 detects the heartbeat from the wrist 60. In the wrist 60, the ulnar artery 63 and the radial artery 64 are respectively located below the ulna 61 and the radius 62 and positioned near a bottom portion of the joined straps 52A and 52B or the fastening mechanism 52C. The two arteries 63 and 64 are substantially perpendicular to the strapping direction of the straps 52A and 52B. As the two arteries 63 and 64 expand as indicated by the dotted lines, the expansion causes the pulsation force in certain directions as indicated by the arrows. Subsequently, as the two arteries 63 and 64 contract, the above expansion force rebounds for a reactive force, and the straps 52A and 52B thus experience a pulsation force. A part of the repeating pulsation force then travels along the straps 52A and 52B towards the heartbeat detection unit 3 via the extended casing portions 51, the extended casing portion 12 and the casing 2.

The extended casing portion 12 and the adjustably extended casing portion 51 extend from the casing 2 at a predetermined angle as indicated by an arrow in order to provide an additional width or horizontal dimension to the casing 2. The predetermined angle and the width of the extended casing portion 12 and the adjustably extended casing portion 51 substantially facilitate the flexible straps 52A and 52B to form a relatively flat portion near the fastening mechanism 52C in order to ascertain snug contact over the bottom portion 60b of the wrist 60 for efficiently initiating the transfer of the pulsation force. The predetermined angle and the predetermined width of the extended casing portion 12 and the adjustably extended casing portion 51 also form the space S2 with the casing 2, the straps 52A and 52B and an upper portion or top portion 60a of the wrist 60 near the heartbeat detection unit 3. The space S2 of FIG. 4 is optionally larger than the space S1 as shown in FIG. 3 since the adjustably extended casing portion 51 and the straps 52A and 52B form an additional space along lateral sides 60S of the wrist 60. Because the extended casing portion 12 and the adjustably extended casing portion 51 are made of hard material, the flexing movement of the wrist 60 is confined in the space S2, and the upper side portions of the wrist 60 fail to touch the corresponding upper side area of the adjustably extended casing portion 51 or the flexible straps 52A and 52B. The lack of the above skin contact thus substantially promotes the efficient transfer of the pulsation force along the straps 52A and 52B and the adjustably extended casing portion 51 towards the heartbeat detection unit 3. Thus, the total width of the casing 2, the extended casing portion 12, the adjustably extended casing portion 51 and the straps 52A and 52B exceeds the width of the wrist 60 in the second preferred embodiment.

Still referring to FIG. 4, the heartbeat detection unit 3 detects the pulsation force that is caused by the arterial expansion and contraction in the wrist 60. The heartbeat detection unit 3 further includes a first chamber 34 and a second chamber 35. Although the first chamber 34 and the second chamber 35 are connected by a communication hole 36a, they are substantially separated by a separation wall 36. The communication hole 36a is located at a substantially central portion of the separation wall 36. A top or ceiling wall of the second chamber 35 is formed by a partially overlapping layer of a pressure sensitive element 38 and a metallic plate 37. A part of the overlapping layer is sandwiched between the separation wall 36 and a panel wall 39 via rubber rings G2. The panel wall 39 has an opening portion 39a, through which lead wires L access the pressure sensitive element 38 and the metallic plate 37. The separation material 36 further includes air-tight protruding portions 36b that extend through the panel wall 39 in order to maintain the internal pressure in the second chamber 35 by pressing the panel wall 39 against the rubber rings G2. The air-tight protruding portions 36b are fused or affixed to the panel wall 39. The first chamber 34 projects towards the wrist 60. A bottom or floor wall 32a and side walls 32b of the first chamber 34 are uniformly or integrally formed by a projection unit 32. The bottom wall 32a is plated by an inflexible plate 33 such as certain hard metal. The projection unit 32 is made of a certain flexible insulation material 31 such as urethane, silicon or synthetic rubber. The insulation material 31 maintains the internal pressure in the first chamber 34. An edge portion of the projection unit 32, the separation wall 36 and the panel wall 39 are screwed together to the casing 2 by the screw N in order to maintain the internal pressure of the heartbeat detection unit 3. To further maintain the internal pressure of the casing 2, the above screwed edge portions are pressed against the rubber rings G1 located near the screw N.

Figure 5:
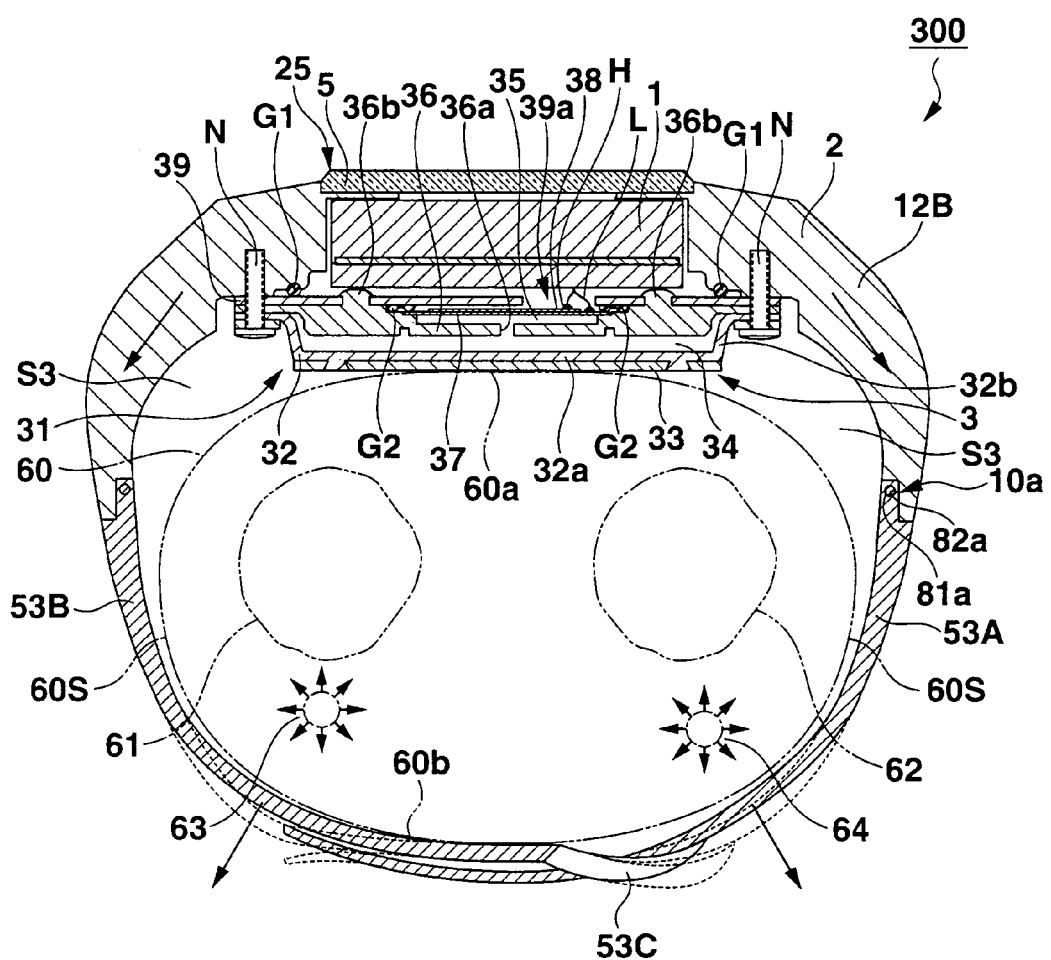
FIG. 5 is a diagram illustrating a cross sectional view of the heartbeat measuring watch device in a third preferred embodiment according to the current invention.

Now referring to FIG. 5, a diagram illustrates a cross sectional view of the heartbeat measuring watch device 300 in a third preferred embodiment according to the current invention. The heartbeat detection unit 3 is mounted on a bottom surface of the time keeping unit 1 that is located in the casing body 2. On the top surface of the time keeping unit 1, a display unit 25 is covered by a transparent watch display cover 5. The heartbeat detection unit 3 is fixed to the casing 2 by components N such as screws via rubber rings G1. An extended casing portion 12B extends from the casing 2 at a predetermined angle as indicated by an arrow in order to provide a predetermined width or horizontal dimension to the casing 2. The extended casing portion 12B further extends downward to form an extended side strap portion 10a. The extended casing portion 12B and the extended side strap portion 10a are made of inflexible material such as hard resin or metal and are integrally formed. The end of the extended side strap portions 10a is removably connected to one end of straps 53A and 53B that are made of flexible, but nonexpandable material such as certain silicon or resin to fit the curvature of a wrist 60 without expansion. At the juncture, the extended side strap portions 10a and the straps 53A and 53B form a connection hole 81a and are connected by a connecting pin 82a in the connection hole 81a. The other end of the straps 53A and 53B has a fastening mechanism 53C such as a buckle to engage with each other so that the heartbeat measuring watch device 300 is adjustably worn around the wrist 60. Thus, the heartbeat detection unit 3 contacts the upper portion or top portion of 60a of the user wrist 60 when the heartbeat measuring watch device 300 is worn as indicated in FIG. 5.

In further detail, the heartbeat measuring watch device 300 detects the heartbeat from the wrist 60. In the wrist 60, the ulnar artery 63 and the radial artery 64 are respectively located below the, ulna 61 and the radius 62 and positioned near a bottom portion of the joined straps 53A and 53B or the fastening mechanism 53C. The two arteries 63 and 64 are substantially perpendicular to the strapping direction of the straps 53A and 53B. As the two arteries 63 and 64 expand as indicated by the dotted lines, the expansion causes the pulsation force in certain directions as indicated by the arrows. Subsequently, as the two arteries 63 and 64 contract, the above expansion force rebounds as a reactive force, and the straps 53A and 53B thus experience a pulsation force. A part of the repeating pulsation force then travels along the straps 53A and 53B towards the heartbeat detection unit 3 via the extended side strap portions 10a, the extended casing portion 12B and the casing 2.

The extended casing portion 12B extends from the casing 2 at a predetermined angle as indicated by an arrow in order to provide an additional width or horizontal dimension to the casing 2. The predetermined angle and the predetermined width of the extended casing portion 12B substantially facilitate the flexible straps 53A and 53B to form a relatively flat portion near the fastening mechanism 53C in order to ascertain snug contact over the bottom portion 60b of the wrist 60 for efficiently initiating the transfer of the pulsation force. The predetermined angle and the predetermined width of the extended casing portion 12B and the extended side strap portions 10a also form the space S3 with the casing 2, the straps 53A and 53B and an upper portion 60a of the wrist 60 near the heartbeat detection unit 3. The space S3 of FIG.

5 is optionally larger than the space S1 as shown in FIG. 3 since the extended side strap portions 10a and the straps 53A and 53B form an additional space along lateral sides 60S of the wrist 60. Because the extended casing portion 12B and the extended side strap portions 10a are made of hard material, the flexing movement of the wrist 60 is confined in the space S3, and the upper side portions of the wrist 60 fail to touch the corresponding upper side area of the extended casing portion 12B, the extended side strap portions 10a or the flexible straps 53A and 53B. The lack of the above skin contact also substantially promotes the efficient transfer of the pulsation force along the straps 53A and 53B, the extended side strap portions 10a and the extended casing portion 12B towards the heartbeat detection unit 3. Thus, the total width of the casing 2, the extended casing portion 12B, the extended side strap portions 10a and the straps 53A and 53B exceeds the width of the wrist 60 in the third preferred embodiment. Alternatively, the extended casing portion 10, the extended side strap portions 10a and the straps 53A and 53B are optionally further broken down to smaller structural pieces.

Still referring to FIG. 5, the heartbeat detection unit 3 detects the pulsation force that is caused by the arterial expansion and contraction in the wrist 60. The heartbeat detection unit 3 further includes a first chamber 34 and a second chamber 35. Although the first chamber 34 and the second chamber 35 are connected by a communication hole 36a, they are substantially separated by a separation wall 36. The communication hole 36a is located at a substantially central portion of the separation wall 36. A top or ceiling wall of the second chamber 35 is formed by a partially overlapping layer of a pressure sensitive element 38 and a metallic plate 37. A part of the overlapping layer is sandwiched between the separation wall 36 and a panel wall 39 via rubber rings G2. The panel wall 39 has an opening portion 39a, through which lead wires L access the pressure sensitive element 38 and the metallic plate 37. The separation material 36 further includes air-tight protruding portions 36b that extend through the panel wall 39 in order to maintain the internal pressure in the second chamber 35 by pressing the panel wall 39 against the rubber rings G2. The air-tight protruding portions 36b are fused or affixed to the panel wall 39. The first chamber 34 projects towards the wrist 60. A bottom or floor wall 32a and side walls 32b of the first chamber 34 are uniformly or integrally formed by a projection unit 32. The bottom wall 32a is plated by an inflexible plate 33 such as certain hard metal. The projection unit 32 is made of a certain flexible insulation material 31 such as urethane, silicon or synthetic rubber. The insulation material 31 maintains the internal pressure in the first chamber 34. An edge portion of the projection unit 32, the separation wall 36 and the panel wall 39 are screwed together to the casing 2 by the screw N in order to maintain the internal pressure of the heartbeat detection unit 3. To further maintain the internal pressure of the casing 2, the above screwed edge portions are pressed against the rubber rings G1 located near the screw N.

Figure 6:
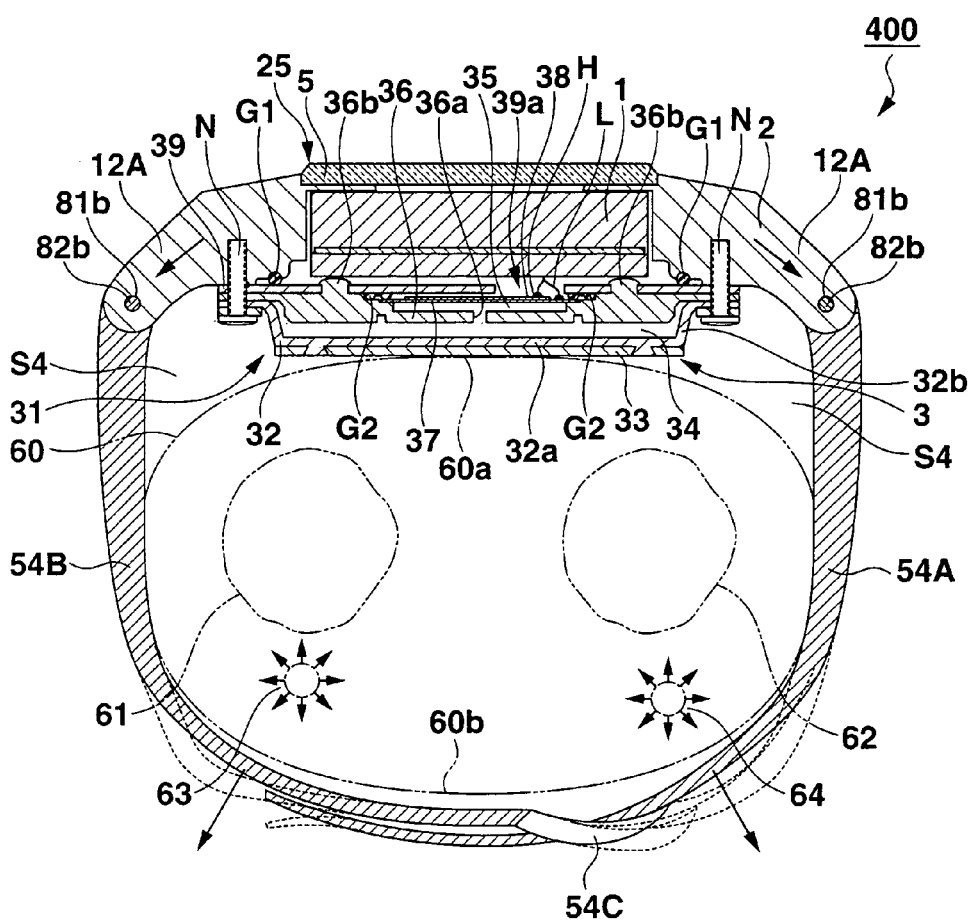
FIG. 6 is a diagram illustrating a cross sectional view of the heartbeat measuring watch device in a fourth preferred embodiment according to the current invention.

Now referring to FIG. 6, a diagram illustrates a cross sectional view of the heartbeat measuring watch device 400 in a fourth preferred embodiment according to the current invention. The heartbeat detection unit 3 is mounted on a bottom surface of the time keeping unit 1 that is located in the casing body 2. On the top surface of the time keeping unit 1, a display unit 25 is covered by a transparent watch display cover 5. The heartbeat detection unit 3 is fixed to the casing 2 by components N such as screws via rubber rings G1. An extended casing portion 12A extends from the casing 2 at a predetermined angle as indicated by an arrow in order to provide a predetermined width or horizontal dimension to the casing 2. The extended casing portion 12A is made of inflexible material such as hard resin or metal and is integrally formed with the casing 2. The end of the extended casing portion 12A is removably connected to one end of straps 54A and 54B that are made of flexible, but non-expandable material such as certain silicon or resin to fit the curvature of a wrist 60 without expansion. At the juncture, the extended casing portion 12A and the straps 54A and 54B form a connection hole 81b and are connected by a connecting pin 82b in the connection hole 81b. The juncture allows some adjustment as the straps 54A and 54B move around the pins 82b. The other end of the straps 54A and 54B has a fastening mechanism 54C such as a buckle to engage with each other so that the heartbeat measuring watch device 400 is adjustably worn around the wrist 60. Thus, the heartbeat detection unit 3 contacts the upper portion or top portion 60a of the user wrist 60 when the heartbeat measuring watch device 400 is worn as indicated in FIG. 6.

In further detail, the heartbeat measuring watch device 400 detects the heartbeat from the wrist 60. In the wrist 60, the ulnar artery 63 and the radial artery 64 are respectively located below the, ulna 61 and the radius 62 and positioned near a bottom portion of the joined straps 54A and 54B or the fastening mechanism 54C. The two arteries 63 and 64 are substantially perpendicular to the strapping direction of the straps 54A and 54B. As the two arteries 63 and 64 expand as indicated by the dotted lines, the expansion causes the pulsation force in certain directions as indicated by the arrows. Subsequently, as the two arteries 63 and 64 contract, the above expansion force rebounds as a reactive force, and the straps 54A and 54B thus experience a pulsation force. A part of the repeating pulsation force then travels along the straps 54A and 54B towards the heartbeat detection unit 3 via the extended casing portion 12A and the casing 2.

The extended casing portion 12A extends from the casing 2 at a predetermined angle as indicated by an arrow in order to provide an additional width or horizontal dimension to the casing 2. The predetermined angle and the predetermined width of the extended casing portion 12A substantially facilitate the flexible straps 54A and 54B to form a relatively flat portion near the fastening mechanism 54C in order to ascertain snug contact over the bottom portion 60b of the wrist 60 for efficiently initiating the transfer of the pulsation force. The predetermined angle and the predetermined width of the extended casing portion 12A also form the space S4 with the casing 2, the straps 54A and 54B and an upper portion or the top portion 60a of the wrist 60 near the heartbeat detection unit 3. Because the extended casing portion 12A is made of hard material, the flexing movement of the wrist 60 is confined in the space S4, and the upper side portions of the wrist 60 fail to touch the corresponding upper side area of the flexible straps 54A and 54B or the extended casing portion 12A. The lack of the above skin contact also substantially promotes the efficient transfer of the pulsation force along the straps 54A and 54B and the extended casing portion 12A towards the heartbeat detection unit 3. Thus, the total width of the casing 2, the extended casing portion 12A and the straps 54A and 54B exceeds the width of the wrist 60 in the fourth preferred embodiment.

Still referring to FIG. 6, the heartbeat detection unit 3 detects the pulsation force that is caused by the arterial expansion and contraction in the wrist 60. The heartbeat detection unit 3 further includes a first chamber 34 and a second chamber 35. Although the first chamber 34 and the second chamber 35 are connected by a communication hole 36a, they are substantially separated by a separation wall 36. The communication hole 36a is located at a substantially central portion of the separation wall 36. A top or ceiling wall of the second chamber 35 is formed by a partially overlapping layer of a pressure sensitive element 38 and a metallic plate 37. A part of the overlapping layer is sandwiched between the separation wall 36 and a panel wall 39 via rubber rings G2. The panel wall 39 has an opening portion 39a, through which lead wires L access the pressure sensitive element 38 and the metallic plate 37. The separation material 36 further includes air-tight protruding portions 36b that extend through the panel wall 39 in order to maintain the internal pressure in the second chamber 35 by pressing the panel wall 39 against the rubber rings G2. The air-tight protruding portions 36b are fused or affixed to the panel wall 39. The first chamber 34 projects towards the wrist 60. A bottom or floor wall 32a and side walls 32b of the first chamber 34 are uniformly or integrally formed by a projection unit 32. The bottom wall 32a is plated by an inflexible plate 33 such as certain hard metal. The projection unit 32 is made of a certain flexible insulation material 31 such as urethane, silicon or synthetic rubber. The insulation material 31 maintains the internal pressure in the first chamber 34. An edge portion of the projection unit 32, the separation wall 36 and the panel wall 39 are screwed together to the casing 2 by the screw N in order to maintain the internal pressure of the heartbeat detection unit 3. To further maintain the internal pressure of the casing 2, the above screwed edge portions are pressed against the rubber rings G1 located near the screw N.

With respect to FIGS. 3, 4, 5 and 6, the first, second, third and fourth preferred embodiments are described to have the heartbeat detection unit 3 on the bottom surface of the time keeping unit 1 that is located in the casing body 2. In an alternative embodiment to the first, second, third or fourth preferred embodiment, the heartbeat detection unit 3 is mounted directly on the strap 4A, 4B, 52A, 52B, 53A and 53B opposite the time keeping unit 1. If the user wears the alternative embodiment as described above with respect to FIGS. 3, 4, 5 and 6, the heartbeat detection unit 3 is located near the ulnar artery 63 and the radial artery 64. In the above described alternative embodiment, other units or portions are correspondingly altered. For example, the heartbeat detection unit 3 is operationally connected to other units such as the CPU 101 in order to transmit electrical signals indicative of the detected heartbeats.

Figure 7A:
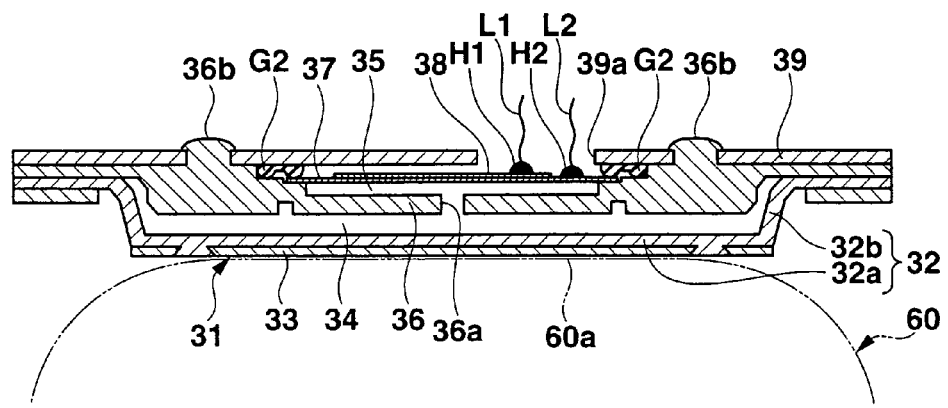
FIG. 7A is a diagram illustrating an enlarged cross sectional view of a first preferred embodiment of the isolated heartbeat detection unit according to the current invention.

Now referring to FIG. 7A, a diagram illustrates an enlarged cross sectional view of a first preferred embodiment of the isolated heartbeat detection unit 3 according to the current invention. The first chamber 34 and the second chamber 35 are formed by the panel wall 39, the separation wall 36 and the projection unit 32. In this preferred embodiment, the first chamber 34 is formed substantially larger than the second chamber 35. The separation wall 36 further includes the air-tight projection portions 36b, which protrude through the panel wall 39 to maintain the internal pressure in the second chamber 35. The projection unit 32 further includes the bottom portion 32a and the side portion 32b that are integrally formed with each other. The hard plate 33 is optionally mounted on an inner bottom surface of the bottom portion 32a. The hard plate 33 is alternatively formed with the bottom portion 32a of the projection unit 32 in an integral manner.

Between the panel wall 39 and the separation wall 36, a thin metallic plate 37 is provided as a flexible body. The metallic plate 37 is located above the communication hole 36a and is placed at the predetermined position by the rubber rings G2 between the separation wall 36 and the panel wall 39. A certain level of the pressure change in the second chamber 35 causes the metallic plate 37 to bend. The pressure sensitive element 38 is mounted on the top of the metallic plate 37, and the pressure sensitive element 38 is formed in a thin circular shape or a disk. The pressure sensitive element 38 and the thin metallic plate 37 output a voltage differential signal indicative of a pressure change in the second chamber 35 to the CPU 101 via lead wires L1 and L2 that are placed through the opening area 39a of the panel wall 39.

Still referring to FIG. 7A, the heartbeat detection unit 3 initially detects the pressure changes at the plate 33 which contacts the wrist 60. As described above, the bottom wall 32a is plated by the inflexible plate 33 such as certain hard metal. Since the metallic plate 33 on the bottom wall 32a fails to flex in response to the arrived pulsation force, the traveled pulsation force in turn depresses and expands the flexible side walls 32b. Consequently, the air pressure in the first chamber 34 is altered due to the depressed or expanded side walls 32b, and the altered air pressure affects the air pressure in the second chamber 35 via the communication hole 36a. The above described pressure change in the second chamber 35 subsequently deforms the metallic plate 37 as well as the pressure sensitive element 38. The pressure sensitive element 38 generates an electrical signal indicative of the pressure change in the second chamber 34.

The communication hole 36a acts as a dumper or a filter to substantially eliminate a high-frequency portion such as noise in the signal generated by the pulsation force. As a air pressure changes in the first chamber 34 due to the noise, the pressure change in the first chamber 34 is transferred through the communication hole 36a. During the limited passage through the communication hole 36a, noise-like high-frequency components are filtered out due to a small amount of transfer at a time, and the air pressure in the second chamber 35 is not substantially affected. Consequently, the pressure sensitive element 38 is not sufficiently deformed to generate a signal indicative of the substantial pressure change in the second chamber 34. Thus, an erroneous noise signal is substantially filtered out for the heartbeat measurement by the communication hole 36a.

Figure 7B:
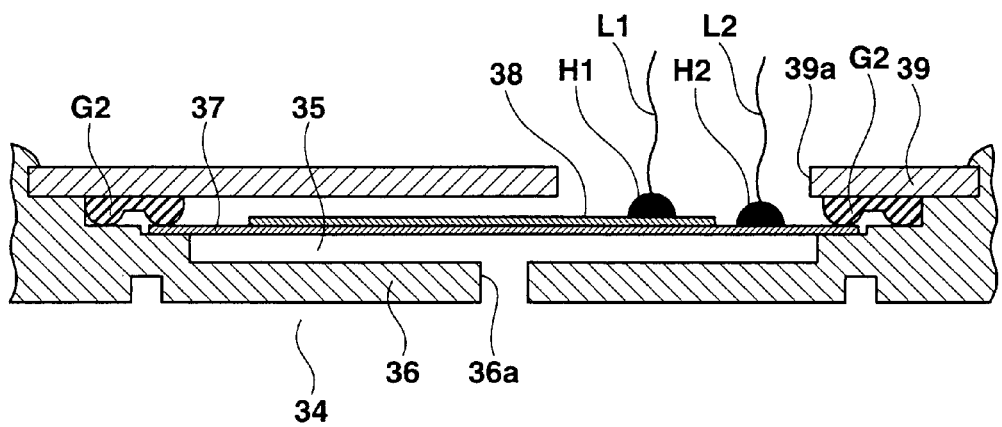
FIG. 7B is a diagram illustrating a further enlarged cross sectional view of the pressure sensitive element and the metallic plate according to the current invention.

Now referring to FIG. 7B, a diagram illustrates a further enlarged cross sectional view of the pressure sensitive element 38 and the metallic plate 37 according to the current invention. A first lead wire L1 is soldered onto the top surface of the pressure sensitive element 38 via a first solder piece H1 and is connected to the CPU 101. Similarly, a second lead wire L2 is soldered onto the top surface of the metallic plate 37 via a second solder piece H2 and is connected to the CPU 101. Thus, the voltage difference is determined between the pressure sensitive element 38 and the metallic plate 37 at the CPU 101.

Figure 8A:
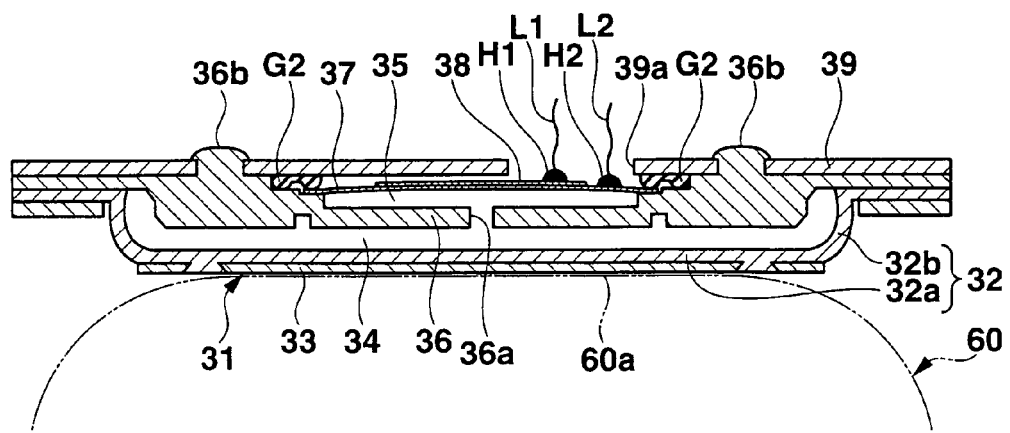
FIG. 8A is a diagram illustrating an enlarged cross sectional view of a second preferred embodiment of the isolated heartbeat detection unit according to the current invention.

Now referring to FIG. 8A, a diagram illustrates an enlarged cross sectional view of a second preferred embodiment of the isolated heartbeat detection unit 3 according to the current invention. The first chamber 34 and the second chamber 35 are formed by the panel wall 39, the separation wall 36 and the projection unit 32. In this preferred embodiment, although the first chamber 34 has a substantially longer length than the second chamber 35 in the horizontal direction, the thickness of the first chamber 34 is not substantially different from that of the second chamber 35 in the vertical direction. The separation wall 36 further includes the air-tight projection portions 36b, which protrude through the panel wall 39 to maintain the internal pressure in the second chamber 35. The projection unit 32 further includes the bottom portion 32a and the side portion 32b that are integrally formed with each other. The plate 33 is optionally mounted on an inner bottom surface of the bottom portion 32a. The plate 33 is alternatively formed with bottom portion 32a of the projection unit 32 in an integral manner.

Between the panel wall 39 and the separation wall 36, a thin metallic plate 37 is provided as a flexible body. The metallic plate is located above the communication hole 36a and is placed at the predetermined position by the rubber rings G2 between the separation wall 36 and the panel wall 39. A certain level of the pressure change in the second chamber 35 causes the metallic plate 37 to bend. The pressure sensitive element 38 is mounted on the top of the metallic plate 37, and the pressure sensitive element 38 is formed in a thin circular shape or a disk. The pressure sensitive element 38 and the thin metallic plate 37 output a voltage differential signal indicative of a pressure change in the second chamber 35 to the CPU 101 via lead wires L1 and L2 that are placed through the opening area 39a of the panel wall 39.

Still referring to FIG. 8A, the heartbeat detection unit 3 initially detects the pressure changes at the plate 33 which contacts the wrist 60. As described above, the bottom wall 32a is plated by the inflexible plate 33 such as certain hard metal. Since the metallic plate 33 on the bottom wall 32a fails to flex in response to the arrived pulsation force, the traveled pulsation force in turn depresses and expands the flexible side walls 32b. Consequently, the air pressure in the first chamber 34 is altered due to the depressed or expanded side walls 32b, and the altered air pressure affects the air pressure in the second chamber 35 via the communication hole 36a. The above described pressure change in the second chamber 35 subsequently deforms the metallic plate 37 as well as the pressure sensitive element 38. The pressure sensitive element 38 generates an electrical signal indicative of the pressure change in the second chamber 34.

The communication hole 36a acts as a dumper or a filter to substantially eliminate a high-frequency portion such as noise in the signal generated by the pulsation force. As a air pressure changes in the first chamber 34 due to the noise, the pressure change in the first chamber 34 is transferred through the communication hole 36a. During the limited passage through the communication hole 36a, noise-like high-frequency components are filtered out due to a small amount of transfer at a time, and the air pressure in the second chamber 35 is not substantially affected. Consequently, the pressure sensitive element 38 is not sufficiently deformed to generate a signal indicative of the substantial pressure change in the second chamber 34. Thus, an erroneous noise signal is substantially filtered out for the heartbeat measurement by the communication hole 36a.

Figure 8B:
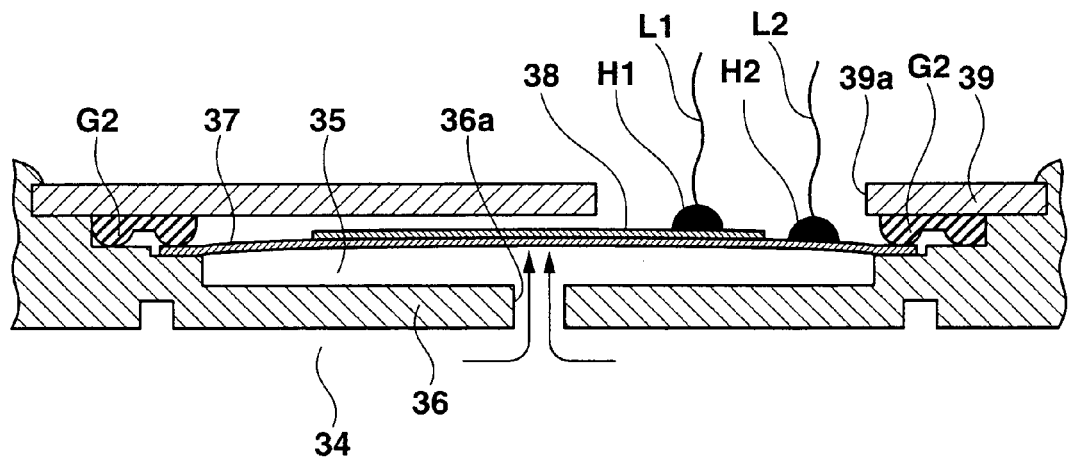
FIG. 8B is a diagram illustrating a further enlarged cross sectional view of the pressure sensitive element and the metallic plate according to the current invention.

Now referring to FIG. 8B, a diagram illustrates a further enlarged cross sectional view of the pressure sensitive element 38 and the metallic plate 37 according to the current invention. A first lead wire L1 is soldered onto the top surface of the pressure sensitive element 38 via a first solder piece H1 and is connected to the CPU 101.

Similarly, a second lead wire L2 is soldered onto the top surface of the metallic plate 37 via a second solder piece H2 and is connected to the CPU 101. Although the metallic plate 37 is held down by the rubber rings G2 at its edge portion, the pressure sensitive elements 38 and the metallic plate 37 are upwardly deformed towards the direction of the panel wall 39 in response to a pressure increase in the second chamber 35. As shown by the arrows, a central portion of the pressure sensitive element 38 and the metallic plate 37 is pushed upwardly while other portions also follow the central portion. The pressure sensitive element 38 outputs an electrical signal indicative of the above described deformation in proportion to an amount of the pressure change. Thus, the voltage difference is determined between the pressure sensitive element 38 and the metallic plate 37 at the CPU 101.

Figure 9:
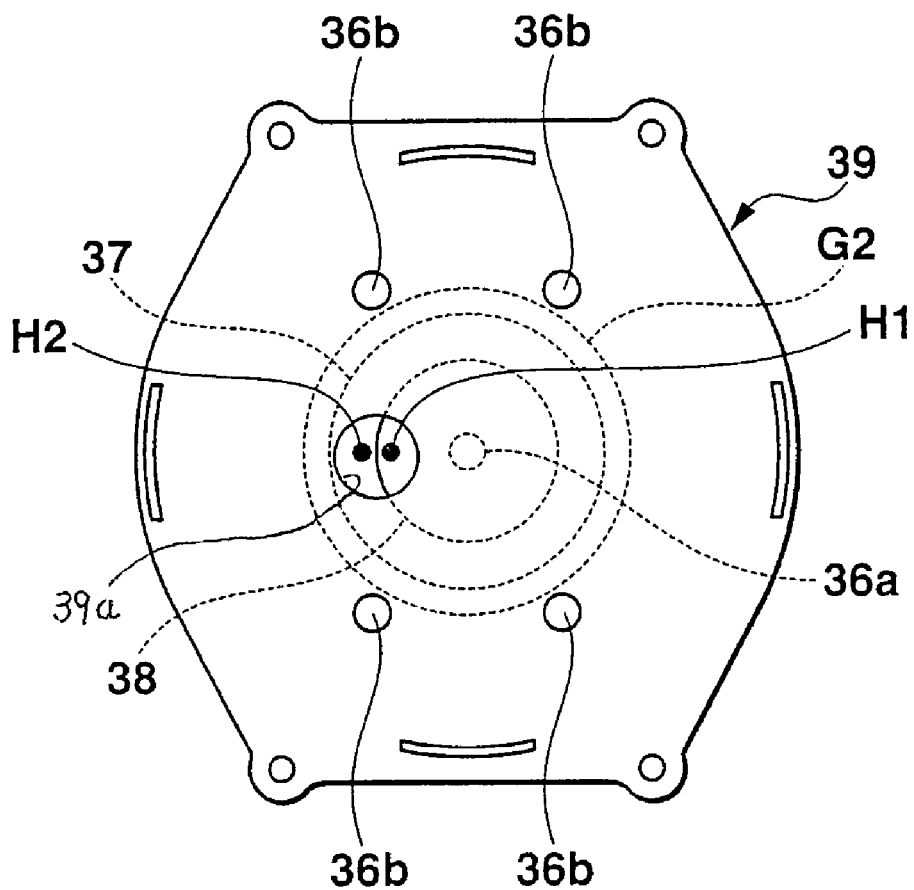
FIG. 9 is a diagram illustrating a top view of the isolated heartbeat detection unit according to the current invention.

Now referring to FIG. 9, a diagram illustrates a top view of the isolated heartbeat detection unit 3 according to the current invention. Four of the air-tight projection portions 36b are shown to protrude through the panel wall 39. With respect to the centrally located communication hole 36a, the pressure sensitive element 38 is concentrically located as both indicated by dotted circular lines. Underneath the pressure sensitive element 38, the metallic plate 37 is also concentrically located as indicated by a corresponding dotted circular line. The rubber rings G2 hold the metallic plate 37 near its edge and are also indicated by a corresponding dotted circular line. The solder H1 and H2 are respectively placed near an edge surface of the pressure sensitive element 38 and the metallic plate 37. In this diagram, the communication hole 39a of FIGS. 7A and 8A is shown by a solid circular line.

Figure 10:
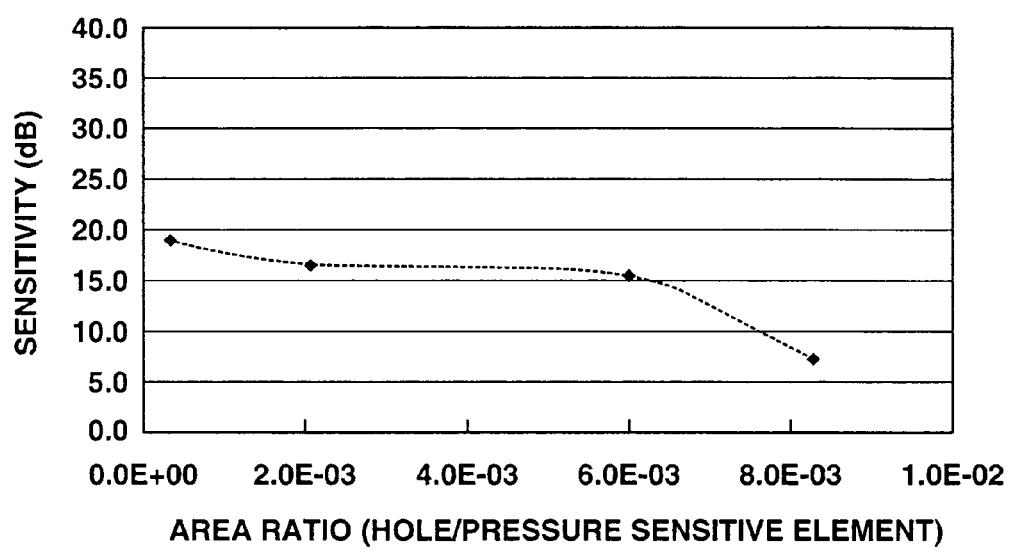
FIG. 10 is a graph illustrating a relationship between the sensitivity of the pressure sensitive element and the size of the communication hole in the heartbeat detection unit according to the current invention.

Now referring to FIG. 10, a graph illustrates a relationship between the sensitivity of the pressure sensitive element 38 and the size of the communication hole 36a in the heartbeat detection unit 3 according to the current invention. The Y axis indicates a sensitivity level of the pressure sensitive element 38 in decibels while the X axis indicates the area ratio of the communication hole 36a to the pressure sensitive element 38, where E is Euler's number. In general, the sensitivity increases as the area of the communication hole 36a becomes smaller with respect to the pressure sensitive element 38. Contrarily, the sensitivity decreases as the area of the communication hole 36a becomes larger with respect to the pressure sensitive element 38. Based upon the above described relation, an accurate heartbeat measurement is obtained by substantially eliminating high-frequency components that are not related to the pulsation force of the heartbeat with an appropriately selected size of the communication hole 36a. For example, if the pressure sensitive element 38 is approximately 20 mm in diameter, the appropriate size of the communication hole 36a is equal to or less than approximately 1 mm in diameter according to the above described relation as shown in FIG. 10. It is also desired to form the communication hole 36a in the center of the panel wall 36.

Figure 11A:
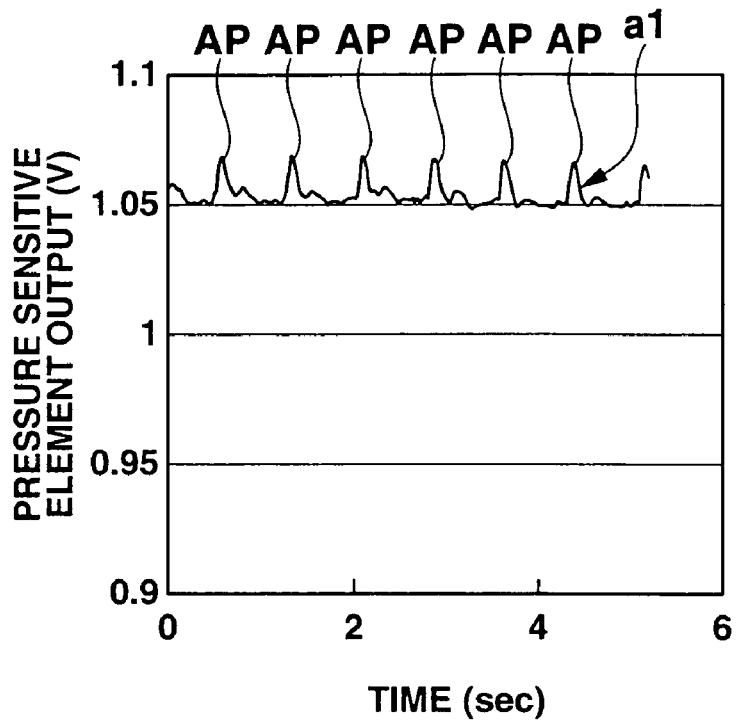
FIGS. 11A and 11B are graphs showing exemplary heartbeat data as measured by the heartbeat measuring watch device in the second preferred embodiment according to the current invention.
Figure 11B:
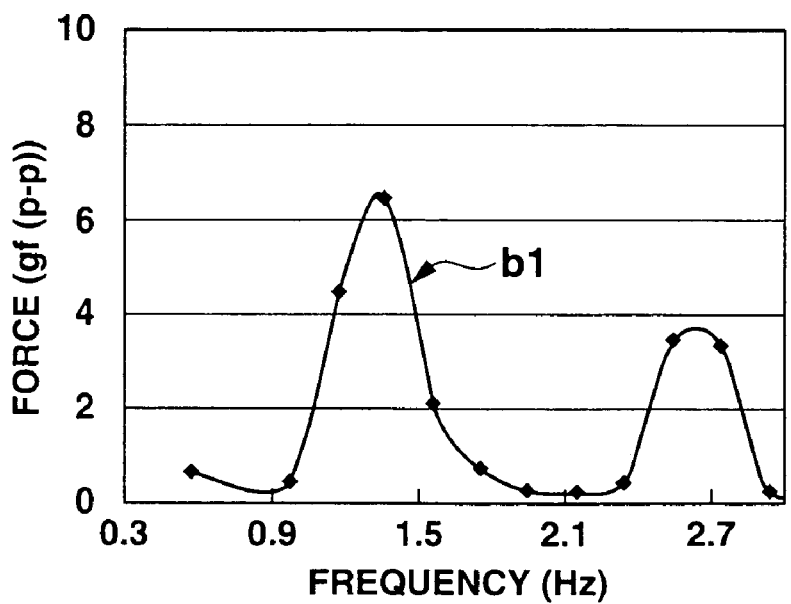

Now referring to FIGS. 11A and 11B, graphs show exemplary heartbeat data as measured by the heartbeat measuring watch device 200 of the second preferred embodiment according to the current invention. In particular, FIG. 11A shows heartbeat pulses or wave forms al that are outputted by the pressure sensitive element 38. The output amplitude is plotted in the X axis while the time in seconds is plotted in the Y axis. A peak of each wave is indicated by a reference AP. The above data was collected from a 31-year male subject wearing the heartbeat measuring watch device 200. FIG. 11B shows a frequency spectrum in hertz (Hz) in the X axis and the force varying strength in gram force (peak-to-peak) gf(p-p) in the Y axis. The above heartbeat pulse output from the pressure sensitive element 38 is converted into force strength values b1 and plotted against the frequency.

Figure 11C:
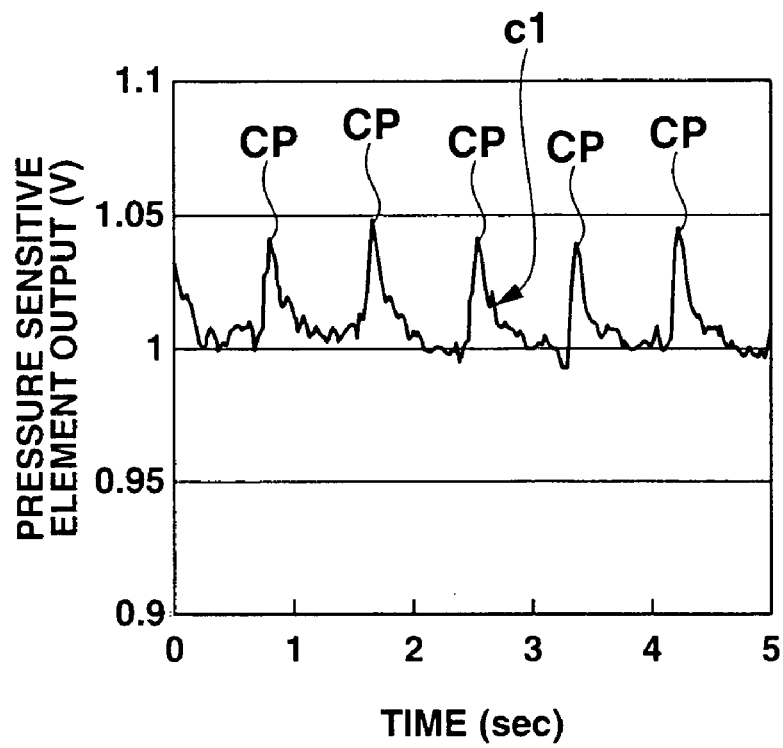
FIGS. 11C and 11D are graphs showing exemplary heartbeat data as measured by the heartbeat measuring watch device in the second preferred embodiment according to the current invention.
Figure 11D:
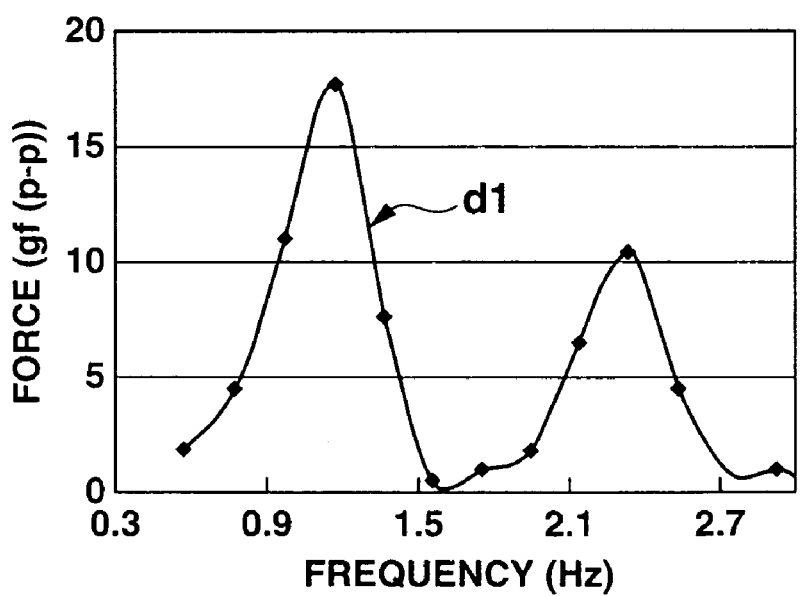

Now referring to FIGS. 11C and 11D, graphs show exemplary heartbeat data as measured by the heartbeat measuring watch device 200 of the second preferred embodiment according to the current invention. In particular, FIG. 11C shows heartbeat pulse or wave forms cl that are outputted by the pressure sensitive element 38. The output amplitude is plotted in the X axis while the time in seconds is plotted in the Y axis. A peak of each wave is indicated by a reference CP. The above data was collected from a 37-year female subject wearing the heartbeat measuring watch device 200. FIG. 11D shows a frequency spectrum in hertz (Hz) in the X axis and the force varying strength in gram force (peak-to-peak) gf(p-p) in the Y axis. The above heartbeat pulse output from the pressure sensitive element 38 is converted into load strength values d1 and plotted against the frequency.

Figure 12:
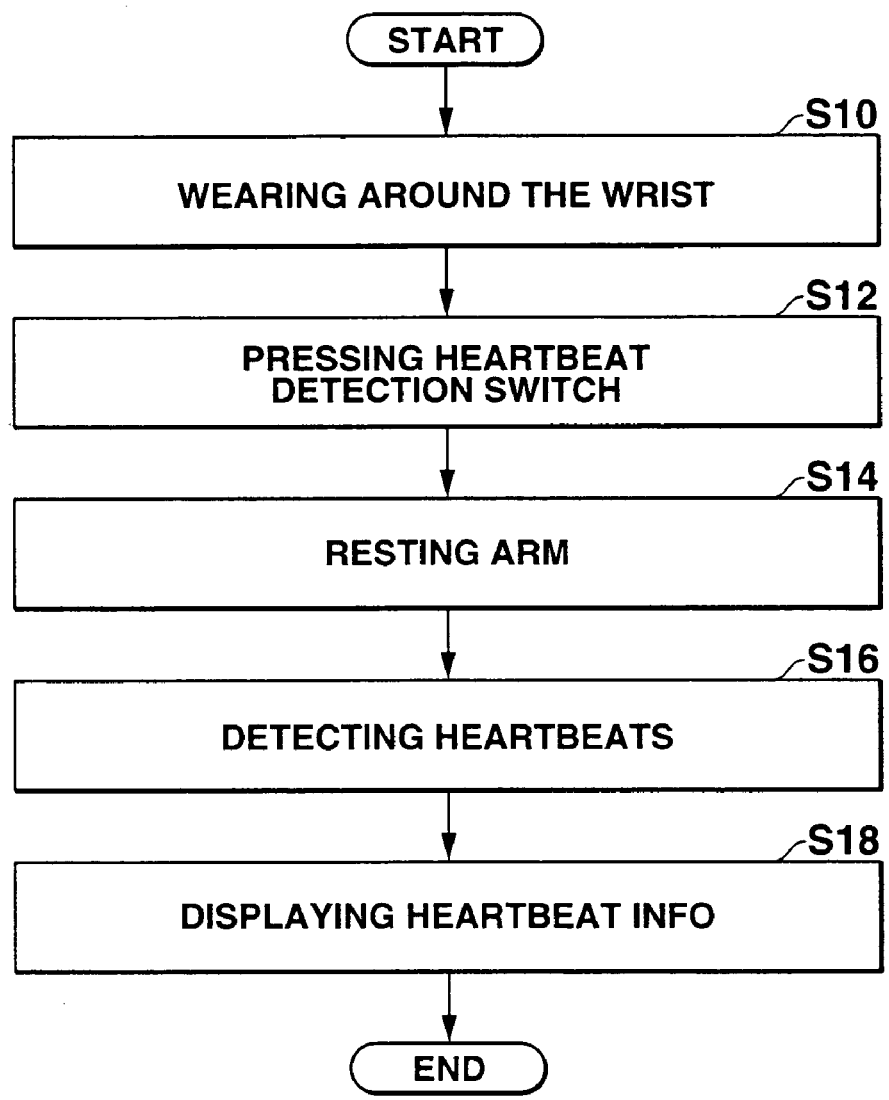
FIG. 12 is a flow chart illustrating general steps involved in a preferred process of monitoring heartbeat according to the current invention.

Now referring to FIG. 12, a flow chart illustrates general steps involved in a preferred process of monitoring heartbeats according to the current invention. Although some components and units are referred in FIGS. 1 and 2 for the following description, the reference is made to facilitate the description of the preferred process and is not made to limit the implementation of the steps. In a step S10, a user wears the heartbeat measuring watch device 100 around his or her wrist. The display unit 25 is placed over the wrist on the back of his hand and is tightened by strap 4 in the step S10. Since the pressure sensor or the heartbeat detection unit 3 is located below the display unit 25, the heartbeat detection unit 3 makes a contact over the wrist on the back hand side rather than the palm side when the heartbeat measuring watch device 100 is worn in the above described manner.

Still referring to FIG. 12, after the heartbeat measuring watch device 100 is substantially immobile over the wrist, the user presses the predetermined switch button 2A on the case 2 in order to initiate a heartbeat measurement in a step S12. The switch buttons 2A1 through 2A4 are connected to the input control unit 102 of FIG. 2 so that the CPU 101 reads a certain software program for the heartbeat measurement from the ROM 106 into the RAM 105 for execution. In a preferred process, a software program is read according to a particular purpose or condition for the heartbeat measurement as indicated by the predetermined switch. For example, in response to a particular switch selection in the step S12, the software program displays a message such as "Be still" or "Relax" in the display unit 25 via the display control unit 103 in a step S14. The heartbeat measurement is, of course, taken during any activities including exercises. For this reason, the above message is meant to be an exemplary and assumes that the user wants to be reminded to have a heartbeat measurement at rest. In any case, the user needs no particular act or needs to war no additional piece for the heartbeat measurement. The software program initiates the heartbeat measurement at the heartbeat detection unit 3 in a step S16. After the heartbeat measurement is completed in the step S16, the measurement result is outputted to a display unit 25 in a step S18. Thus, the preferred process of monitoring the heartbeat is completed.

Figure 13:
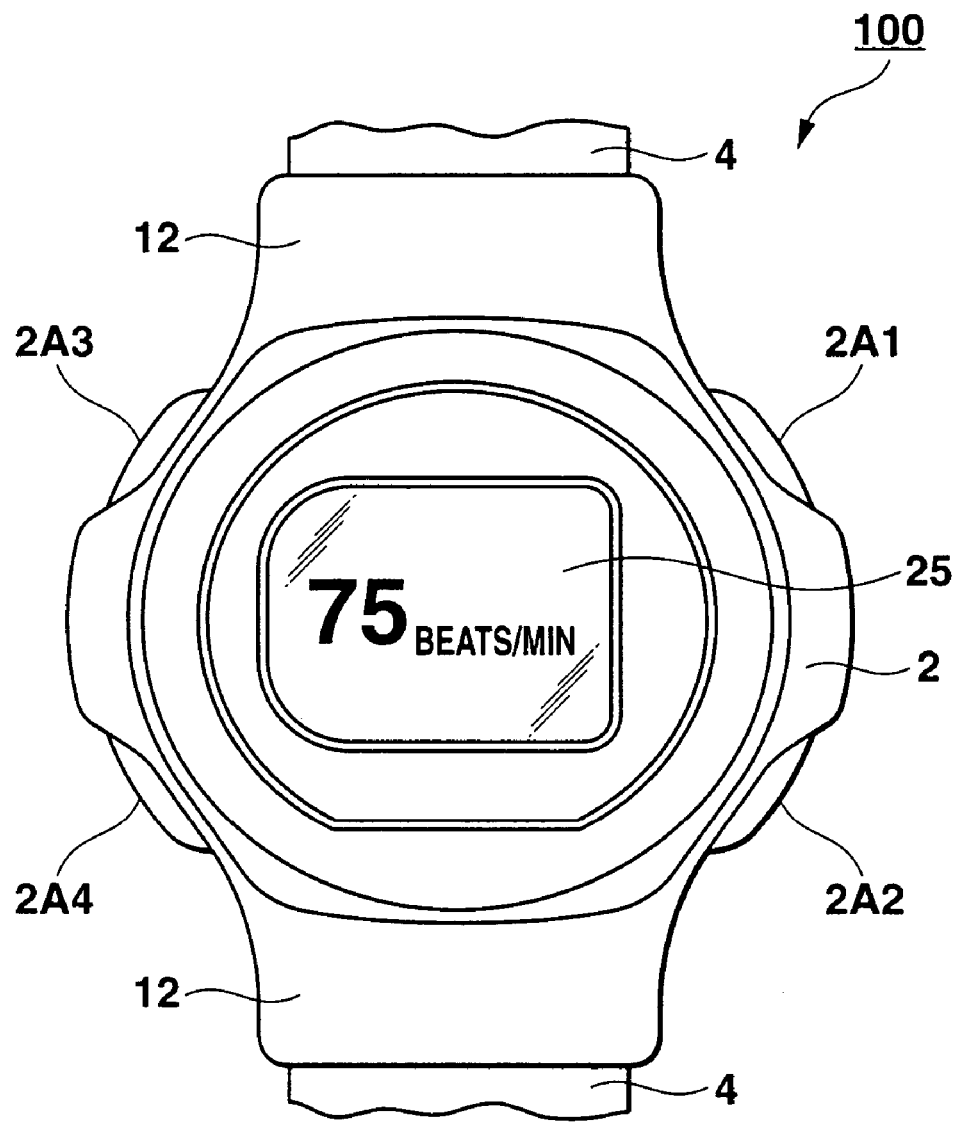
FIG. 13 is a diagram illustrating an exemplary display output of a heartbeat measurement result according to the current invention.

Now referring to FIG. 13, a diagram illustrates an exemplary display output of a heartbeat measurement result according to the current invention. The display unit 25 is mounted on the front surface of the watch casing 2 between the straps 4. The display unit generally indicates information that is determined by a default mode. In one setting, the default mode specifies that time and date are displayed. In another setting, the default mode specifies to display continuous heartbeat information. The default setting is modified by a combination of the inputs from the key switches 2A1, 2A2, 2A3 and 2A4. After the heartbeat measurement is completed as described with respect to the step S16 of FIG. 3, the user is notified of the completion either by an audible sound and or a display. The display is optionally flashed for some time and includes the measurement result such as shown in a number of heartbeats per minute. In this example, 75 heartbeats per minute is displayed as a measurement result. After a predetermined amount of time, the display is automatically changed to a default display in a preferred embodiment. Alternatively, the displayed result remains until the user presses a predetermined switch.

Figure 14:
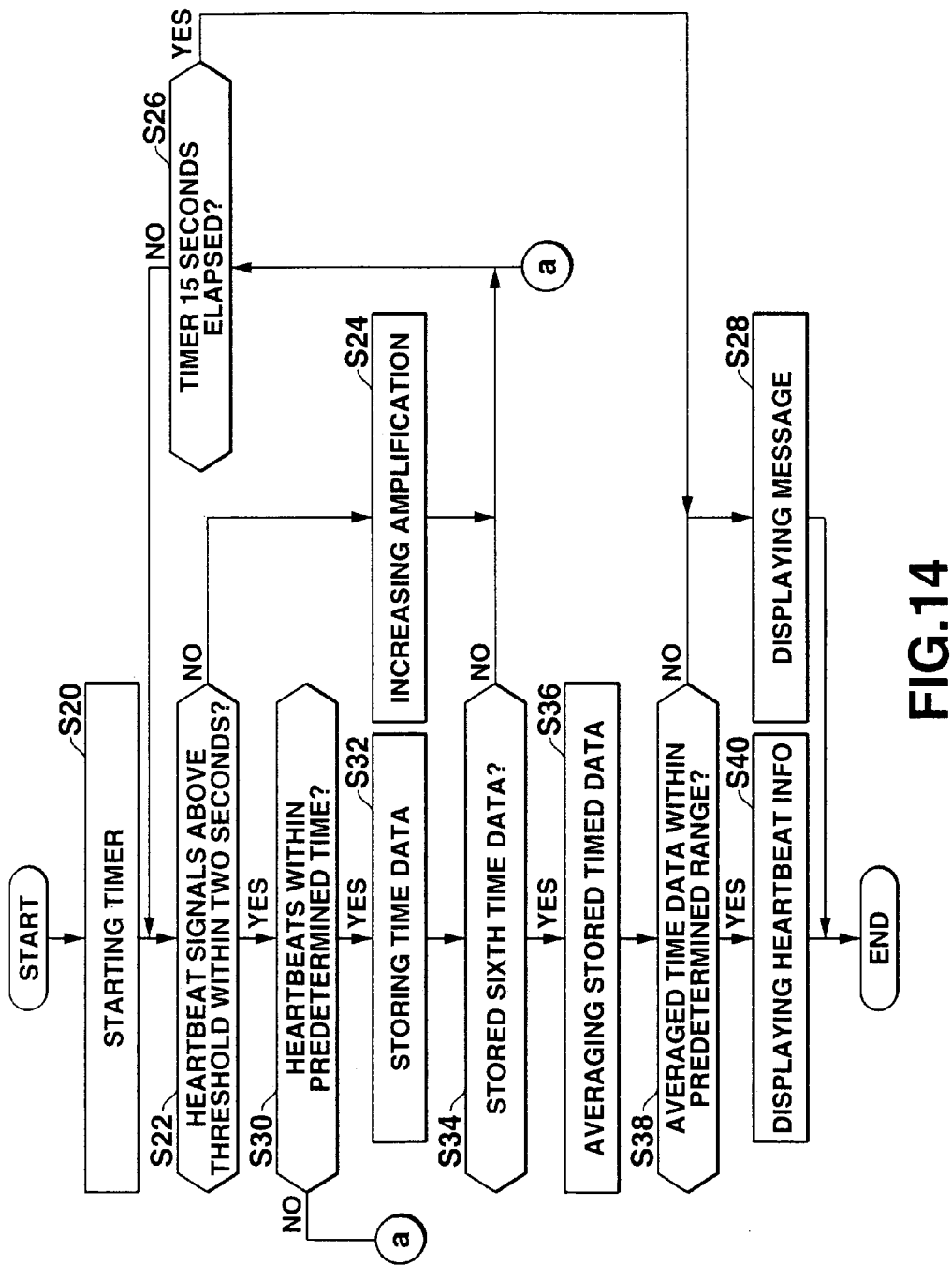
FIG. 14 is a flow chart illustrating detailed steps involved in a preferred process of monitoring heartbeat according to the current invention.

Now referring to FIG. 14, a flow chart illustrates detailed steps involved in a preferred process of monitoring heartbeat according to the current invention. Although some components and units are referred in FIGS. 1 and 2 for the following description, the reference is made to facilitate the description of the preferred process and is not made to limit the implementation of the steps. In general, the following steps illustrated in FIG. 14 further describe the steps S16 and S18 of FIG. 12. In a step S20, a user initiates a heartbeat measurement by pressing a predetermined switch. Upon the user initiation command, a predetermined timer is started in a step S20. In a step S22, it is determined whether or not heartbeat signals beyond a predetermined threshold level are detected within two seconds based upon heartbeat wave signals. If it is determined in the step S22 that the above specified signals are not detected within two seconds, the amplification of the heartbeat measuring signal is increased in a step S24. Subsequently, it is further determined in a step S26 whether or not fifteen seconds have elapsed since the onset of the timer in the step S20. If it is determined in the step S26 that fifteen seconds have not yet elapsed, the preferred process continues at the step S22. On the other hand, if it is determined in the step S26 that fifteen seconds have already elapsed, the preferred process proceeds to a step S28, where an error message is displayed and subsequently terminates.

Still referring to FIG. 14, the steps will be described following a successful detection of the heartbeat signals in the step 22. If it is determined in the step S22 that the above specified signals are detected within two seconds, it is further determined in a step S30 whether or not an interval between the consecutively detected heartbeat signals is within a predetermined amount of time. If it is determined in the step 30 that the interval is not within a predetermined amount of time, the preferred process proceeds to the step S26 and follows the above described steps. On the other hand, if it is determined in the step 30 that the interval is within a predetermined amount of time, the detected interval time data is stored in memory in a step S32. In a subsequent step 34, it is further determined whether or not the six time intervals have been stored in the memory. If it is determined in the step S34 that the six intervals have not been stored, the preferred process proceeds to the step S26 and follows the above described steps. On the other hand, if it is determined in the step S36 that the six intervals have been stored, an average interval value is calculated among the six stored intervals in a step S36. Lastly, it is determined in a step S38 whether or not the average interval value is within a predetermined range, which is from approximately 300 ms or 200 beats per minute to approximately 2000 ms or 30 beats per minute. If it is determined in the step S38 that the average interval value is not within the predetermined range, an error message is displayed in a step S28 and the preferred process terminates. On the other hand, if it is determined in the step S38 that the average interval value is within the predetermined range, the measured heartbeat information is displayed in a step S40, and the preferred process terminates.

Figure 15:
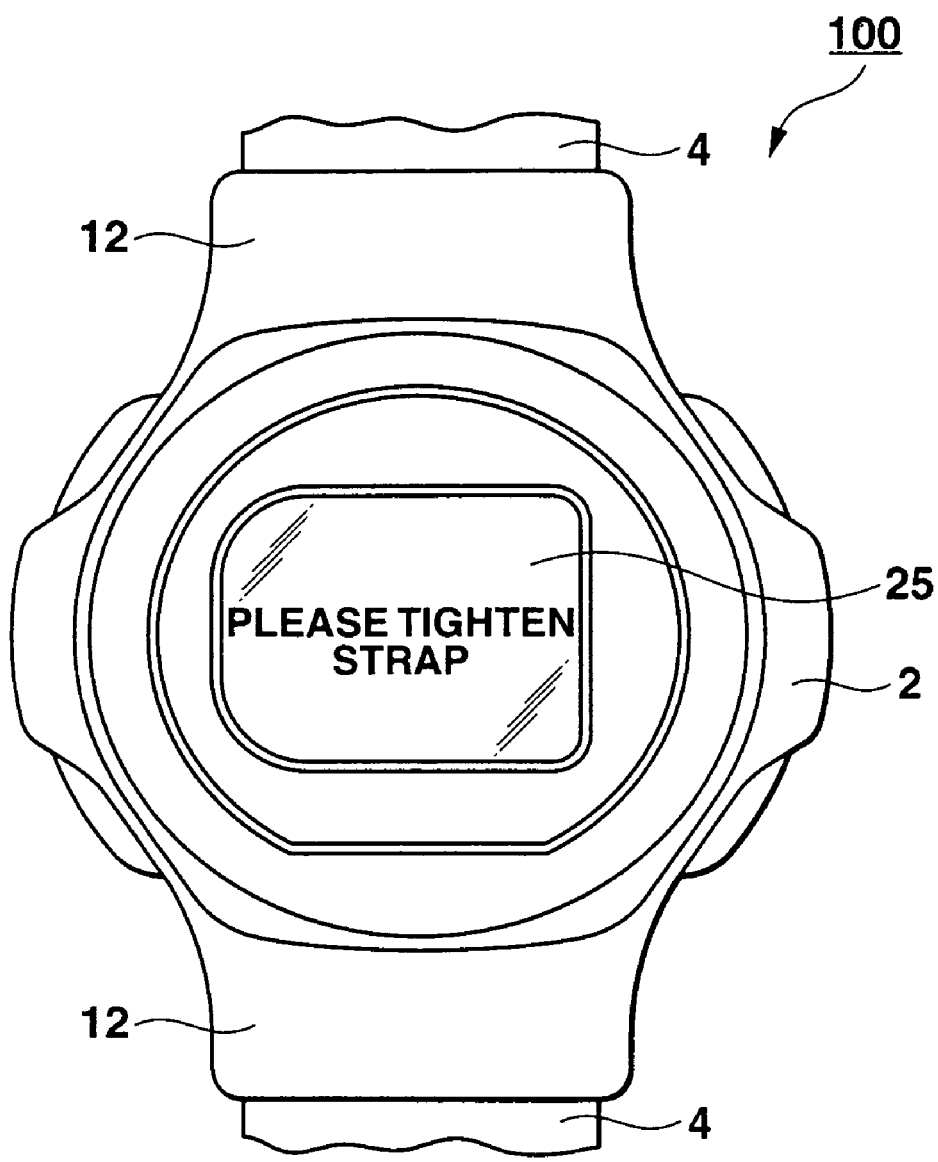
FIG. 15 is a diagram illustrating an exemplary message that is displayed on the display unit of the heartbeat measuring watch device during the heartbeat measurement according to the current invention.

Now referring to FIG. 15, a diagram illustrates an exemplary message that is displayed on the display unit 25 of the heartbeat measuring watch device 100 during the heartbeat measurement according to the current invention. As described above with respect to FIG. 14, the heartbeat measurement is displayed only when the measured data satisfies a predetermined set of requirements. For example, even if certain requirements are met, when fifteen seconds have elapsed as indicated in the step S26 since the data collection started, an error message is displayed in the step S28. Similarly, when the averaged interval of the measured signals exceeds the predetermined range, the error message is also displayed in the step S28. One of the error messages is shown in FIG. 15 to advise the user to "tighten the strap" before another heartbeat measurement. Pulsation force is caused by the expanding/contracting arteries in the wrist, and the pulsation force is transferred onto the strap. When the strap is not sufficiently tightened around the wrist of the user during the heartbeat measurement, adequate heartbeat signals are not sampled by the heartbeat detection unit 3 since undesirable space between the wrist and the strap prevents the pulsation force from traveling the strap to the heartbeat detection unit 3. The tightly worn strap promotes some tension in the strap so that the pulsation force efficiently travels along the strap towards the heartbeat detection unit 3.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A wearable heartbeat measuring device, comprising:
    a heartbeat detection unit for detecting an arterial movement indicative of a heartbeat around the wrist to generate a heartbeat signal; and
    a wrist strap for supporting said heartbeat detection unit near a top portion of the wrist, said wrist strap having a flexible portion and an inflexible portion, said inflexible portion extending from said heartbeat detection unit and having a predetermined angle and a predetermined width with respect to the wrist so as to form a predetermined amount of space between the wrist and said strap near the top portion of the wrist, said inflexible portion further including a first adjustable portion having a plurality of holes and a pin for adjusting the width.

2. The wearable heartbeat measuring device according to claim 1 wherein said flexible portion and the wrist form the space.

3. The wearable heartbeat measuring device according to claim 1 wherein said flexible portion further includes a second adjustable portion.

4. The wearable heartbeat measuring device according to claim 1 wherein said flexible portion is connected to said inflexible portion and has a fastening mechanism for adjustment.

5. The wearable heartbeat measuring device according to claim 4 wherein said inflexible portion places said flexible portion so as to form a substantially flat area that is located opposite to said heartbeat detection unit.

6. The wearable heartbeat measuring device according to claim 5 wherein said flexible portion receives pulsation force that is caused by the arterial movement and transmits the pulsation force towards said heartbeat detection unit via said inflexible portion.

7. The wearable heartbeat measuring device according to claim 1 wherein a width of said flexible portion and said inflexible portion exceeds a width of the wrist.

8. The wearable heartbeat measuring device according to claim 1 wherein said heartbeat detection unit further includes a first chamber and a second chamber that is connected to said first chamber via a communication hole.

9. The wearable heartbeat measuring device according to claim 1 further comprising:
    a clock unit located adjacent to said heartbeat detection unit for keeping time;
    a processing unit connected to said heartbeat detection unit for processing the heartbeat signal from said heartbeat detection unit to generate the heartbeat result; and
    a display unit connected to said clock unit and said processing unit for selectively displaying the time and the heartbeat result.

10. A heartbeat detection device, comprising:
    a first unit having a first flexible enclosed area for forming a first chamber, a pressure in said first chamber changing in response to an externally applied pressure, said first unit further including an inflexible plate mounted on a surface where the externally applied pressure is exerted;
    a second unit having a second enclosed area located adjacent to said first chamber for forming a second chamber, said second chamber having a pressure sensitive element for generating a signal indicative of a pressure change; and
    a separation wall located between said first unit and said second unit, said separation wall having a communication hole for connecting said first chamber and said second chamber.

11. The heartbeat detection device according to claim 10 wherein said first chamber is larger than said second chamber.

12. The heartbeat detection device according to claim 10 wherein said second unit further includes a metallic plate that is placed between said pressure sensitive element and said second chamber.

13. A wearable heartbeat measuring device, comprising:
    a heartbeat detection unit for detecting an arterial movement indicative of a heartbeat around the wrist to generate a heartbeat signal; and
    a wrist strap for supporting said heartbeat detection unit near a top portion of the wrist, said wrist strap having a flexible portion and an inflexible portion, said inflexible portion extending from said heartbeat detection unit and having a predetermined angle and a predetermined width that exceeds the wrist so as to form a predetermined amount of space between the wrist and said strap near the top portion of the wrist, said inflexible portion further including a first adjustable portion having a plurality of holes and a pin for adjusting the width.

14. The wearable heartbeat measuring device according to claim 13 wherein said flexible portion further includes a second adjustable portion.

15. The wearable heartbeat measuring device according to claim 13 wherein said flexible portion is connected to said inflexible portion and has a fastening mechanism for adjustment.

16. The wearable heartbeat measuring device according to claim 15 wherein said inflexible portion places said flexible portions so as to form a substantially flat area that is located opposite to said heartbeat detection unit.

17. The wearable heartbeat measuring device according to claim 16 wherein said flexible portion receives pulsation force that is caused by the arterial movement and transmits the pulsation force towards said heartbeat detection unit via said inflexible portion.

18. The wearable heartbeat measuring device according to claim 13 wherein said heartbeat detection unit further includes a first chamber and a second chamber that is connected to said first chamber via a communication hole.

19. The wearable heartbeat measuring device according to claim 13 further comprising:

a clock unit located adjacent to said heartbeat detection unit for keeping time;

a processing unit connected to said heartbeat detection unit for processing the heartbeat signal from said heartbeat detection unit to generate the heartbeat result; and a display unit connected to said clock unit and said processing unit for selectively displaying the time and the heartbeat result.

20. The wearable heartbeat measuring device according to claim 13 wherein said flexible portion and the wrist form the space.

* * * * *